US011241198B2

(12) United States Patent
Blomqvist et al.

(10) Patent No.: US 11,241,198 B2
(45) Date of Patent: Feb. 8, 2022

(54) METHOD AND APPARATUS FOR SYNCHRONIZING IMPEDANCE CARDIOGRAPHY WITH ELECTROCARDIOGRAPHY TO LOWER PATIENT AUXILIARY CURRENT

(71) Applicant: Nokia Technologies Oy, Espoo (FI)

(72) Inventors: Kim Blomqvist, Espoo (FI); Mikko Honkala, Espoo (FI); Harri Lindholm, Helsinki (FI)

(73) Assignee: Nokia Technologies Oy, Espoo (FI)

(*) Notice: Subject to any disclaimer, the term of this patent is extended or adjusted under 35 U.S.C. 154(b) by 104 days.

(21) Appl. No.: 16/332,256

(22) PCT Filed: Sep. 20, 2016

(86) PCT No.: PCT/FI2016/050649
§ 371 (c)(1),
(2) Date: Mar. 11, 2019

(87) PCT Pub. No.: WO2018/055228
PCT Pub. Date: Mar. 29, 2018

(65) Prior Publication Data
US 2019/0200939 A1    Jul. 4, 2019

(51) Int. Cl.
*A61B 5/00*      (2006.01)
*A61B 5/0535*   (2021.01)
(Continued)

(52) U.S. Cl.
CPC .......... *A61B 5/7285* (2013.01); *A61B 5/0535* (2013.01); *A61B 5/349* (2021.01); *A61B 5/366* (2021.01); *A61B 5/7264* (2013.01)

(58) Field of Classification Search
CPC ... A61B 5/7285; A61B 7/0452; A61B 5/0472; A61B 5/0535; A61B 5/7264
See application file for complete search history.

(56) References Cited

U.S. PATENT DOCUMENTS 6,449,509 B1 * 9/2002 Park .................... A61N 1/36521
                                                               600/533
7,783,345 B2 * 8/2010 Skrabal ................ A61B 5/0535
                                                               600/547
(Continued)

FOREIGN PATENT DOCUMENTS

EP          1275342          1/2003
WO      WO99/55228        11/1999
(Continued)

OTHER PUBLICATIONS

International Search Report for International Patent Application No. PCT/FI2016/050649 dated Dec. 30, 2016, 6 pages.
(Continued)

*Primary Examiner* — Christopher A Flory
(74) *Attorney, Agent, or Firm* — Locke Lord LLP

(57) ABSTRACT

An approach is provided for synchronizing an impedance cardiography ("ICG") measurement period with an electrocardiography ("ECG") signal to reduce patient (105) auxiliary current. The approach involves measuring an ECG signal of a patient via an ECG device (103). The approach also involves processing the ECG signal to cause, at least in part, a detection of one or more ECG features of the signal. The approach further involves synchronizing a start, a stop, or a combination thereof of a measurement of an ICG signal of the patient via an ICG device (101) based, at least in part, on the detection of the one or more ECG features. The measurement of the ICG signal includes injecting an electrical current into the patient (105) for a duration of the measurement.

18 Claims, 14 Drawing Sheets

(51) Int. Cl.
*A61B 5/349* (2021.01)
*A61B 5/366* (2021.01)

(56) References Cited

U.S. PATENT DOCUMENTS

| | | | | |
|---|---|---|---|---|
| 2006/0111641 | A1* | 5/2006 | Manera | A61B 5/411 600/513 |
| 2009/0030292 | A1* | 1/2009 | Bartnik | A61B 7/00 600/301 |
| 2010/0094147 | A1* | 4/2010 | Inan | A61B 5/0006 600/500 |
| 2012/0022336 | A1* | 1/2012 | Teixeira | A61B 5/0205 600/300 |
| 2012/0022844 | A1* | 1/2012 | Teixeira | A61B 5/0205 703/11 |
| 2012/0041279 | A1* | 2/2012 | Freeman | A61B 5/053 600/301 |
| 2014/0309540 | A1* | 10/2014 | Morikawa | A61B 5/0826 600/484 |
| 2016/0135706 | A1* | 5/2016 | Sullivan | A61B 5/1118 600/301 |
| 2016/0361041 | A1* | 12/2016 | Barsimantov | G16H 50/30 |
| 2017/0188890 | A1* | 7/2017 | Banet | A61B 5/0205 |
| 2019/0012608 | A1* | 1/2019 | Teixeira | G16H 50/30 |
| 2019/0357854 | A1* | 11/2019 | Reich | A61B 5/029 |

FOREIGN PATENT DOCUMENTS

| | | |
|---|---|---|
| WO | WO2011120973 | 10/2011 |
| WO | WO2016022941 | 2/2016 |

OTHER PUBLICATIONS

Written Opinion of the International Searching Authority for International Patent Application No. PCT/FI2016/050649 dated Dec. 30, 2016, 8 pages.

Extended European Search Report for European Patent Application No. 16916714.5 dated Jan. 23, 2020, 11 pages.

* cited by examiner

METHOD AND APPARATUS FOR SYNCHRONIZING IMPEDANCE CARDIOGRAPHY WITH ELECTROCARDIOGRAPHY TO LOWER PATIENT AUXILIARY CURRENT

BACKGROUND

Vital sign monitoring, particularly of the heart and vascular system, has become increasingly popular with patients and consumers. For example, techniques such as impedance cardiography ("ICG", sometimes also referred as impedance plethysmography "IPG", or electrical impedance plethysmography "EIP") and electrocardiography ("ECG") can give highly accurate measurements of the mechanical and electrical properties of the heart and vascular system. ICG, for instance, intentionally injects electrical current (e.g., representing auxiliary current) into a patient's body to measure the electrical conductivity of the thorax and its changes in time. These enables the analysis of the heart's mechanical properties (e.g., pre-ejection period ("PEP"), ventricular ejection time ("VET"), stroke volume, heart rate, cardiac output, etc.), while ECG measures the electrical activity of the heart as the heartbeats over time without providing such current. Generally, the accuracy or sensitivity of ICG measurements is dependent on the level of electrical current injected into the patient (e.g., higher currents yield better signal-to-noise ratio). However, patient safety regulations typically limit how much of this auxiliary current can be passed through a patient. Accordingly, device manufacturers face significant technical challenges in ensuring patient safety while also ensuring accurate and relevant health monitoring data from ICG and ECG devices.

SOME EXAMPLE EMBODIMENTS

Therefore, there is a need for an approach for synchronizing an ICG measurement period with an ECG signal to reduce patient auxiliary current.

According to one embodiment, a method comprises measuring an ECG signal of a patient via an ECG device. The method also comprises processing the ECG signal to cause, at least in part, a detection of one or more ECG features of the signal. The method further comprises synchronizing a start, a stop, or a combination thereof of a measurement of an ICG signal of the patient via an ICG device based, at least in part, on the detection of the one or more ECG features. The measurement of the ICG signal includes injecting an electrical current into the patient for a duration of the measurement.

According to another embodiment, an apparatus comprises at least one processor, and at least one memory including computer program code for one or more computer programs, the at least one memory and the computer program code configured to, with the at least one processor, cause, at least in part, the apparatus to measure an ECG signal of a patient via an ECG device. The apparatus is also caused to process the ECG signal to cause, at least in part, a detection of one or more ECG features of the signal. The apparatus is further caused to synchronize a start, a stop, or a combination thereof of a measurement of an ICG signal of the patient via an ICG device based, at least in part, on the detection of the one or more ECG features. The measurement of the ICG signal includes injecting an electrical current into the patient for a duration of the measurement.

According to another embodiment, a computer-readable storage medium carries one or more sequences of one or more instructions which, when executed by one or more processors, cause, at least in part, an apparatus to measure an ECG signal of a patient via an ECG device. The apparatus is also caused to process the ECG signal to cause, at least in part, a detection of one or more ECG features of the signal. The apparatus is further caused to synchronize a start, a stop, or a combination thereof of a measurement of an ICG signal of the patient via an ICG device based, at least in part, on the detection of the one or more ECG features. The measurement of the ICG signal includes injecting an electrical current into the patient for a duration of the measurement.

According to another embodiment, an apparatus comprises means for measuring an ECG signal of a patient via an ECG device. The apparatus also comprises means for processing the ECG signal to cause, at least in part, a detection of one or more ECG features of the signal. The apparatus further comprises means for synchronizing a start, a stop, or a combination thereof of a measurement of an ICG signal of the patient via an ICG device based, at least in part, on the detection of the one or more ECG features. The measurement of the ICG signal includes injecting an electrical current into the patient for a duration of the measurement.

According to another embodiment, a system comprises an ECG device configured to measure an ECG signal of a patient. The system also comprises an ICG device configured to measure an ICG signal of the patient. The measurement of the ICG signal includes injecting an electrical current into the patient for a duration of the measurement. The system further comprises a synchronizing module configured to process the ECG signal to cause, at least in part, a detection of one or more ECG features of the signal, and to synchronize a start, a stop, or a combination thereof of the measurement of an impedance cardiography (ICG) signal of the patient via an ICG device based, at least in part, on the detection of the one or more ECG features.

In addition, for various example embodiments of the invention, the following is applicable: a method comprising facilitating a processing of and/or processing (1) data and/or (2) information and/or (3) at least one signal, the (1) data and/or (2) information and/or (3) at least one signal based, at least in part, on (or derived at least in part from) any one or any combination of methods (or processes) disclosed in this application as relevant to any embodiment of the invention.

For various example embodiments of the invention, the following is also applicable: a method comprising facilitating access to at least one interface configured to allow access to at least one service, the at least one service configured to perform any one or any combination of network or service provider methods (or processes) disclosed in this application.

For various example embodiments of the invention, the following is also applicable: a method comprising facilitating creating and/or facilitating modifying (1) at least one device user interface element and/or (2) at least one device user interface functionality, the (1) at least one device user interface element and/or (2) at least one device user interface functionality based, at least in part, on data and/or information resulting from one or any combination of methods or processes disclosed in this application as relevant to any embodiment of the invention, and/or at least one signal resulting from one or any combination of methods (or processes) disclosed in this application as relevant to any embodiment of the invention.

For various example embodiments of the invention, the following is also applicable: a method comprising creating and/or modifying (1) at least one device user interface element and/or (2) at least one device user interface functionality, the (1) at least one device user interface element and/or (2) at least one device user interface functionality based at least in part on data and/or information resulting from one or any combination of methods (or processes) disclosed in this application as relevant to any embodiment of the invention, and/or at least one signal resulting from one or any combination of methods (or processes) disclosed in this application as relevant to any embodiment of the invention.

In various example embodiments, the methods (or processes) can be accomplished on the service provider side or on the mobile device side or in any shared way between service provider and mobile device with actions being performed on both sides.

For various example embodiments, the following is applicable: An apparatus comprising means for performing the method of any of the claims.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The embodiments of the invention are illustrated by way of example, and not by way of limitation, in the figures of the accompanying drawings.

DESCRIPTION OF SOME EMBODIMENTS

Examples of a method, apparatus, and computer program for synchronizing a measurement period of an impedance cardiography ("ICG") signal with an electrocardiography ("ECG") feature to reduce patient auxiliary current are disclosed. In the following description, for the purposes of explanation, numerous specific details are set forth in order to provide a thorough understanding of the embodiments of the invention. It is apparent, however, to one skilled in the art that the embodiments of the invention may be practiced without these specific details or with an equivalent arrangement. In other instances, well-known structures and devices are shown in block diagram form in order to avoid unnecessarily obscuring the embodiments of the invention.

Figure 1A:
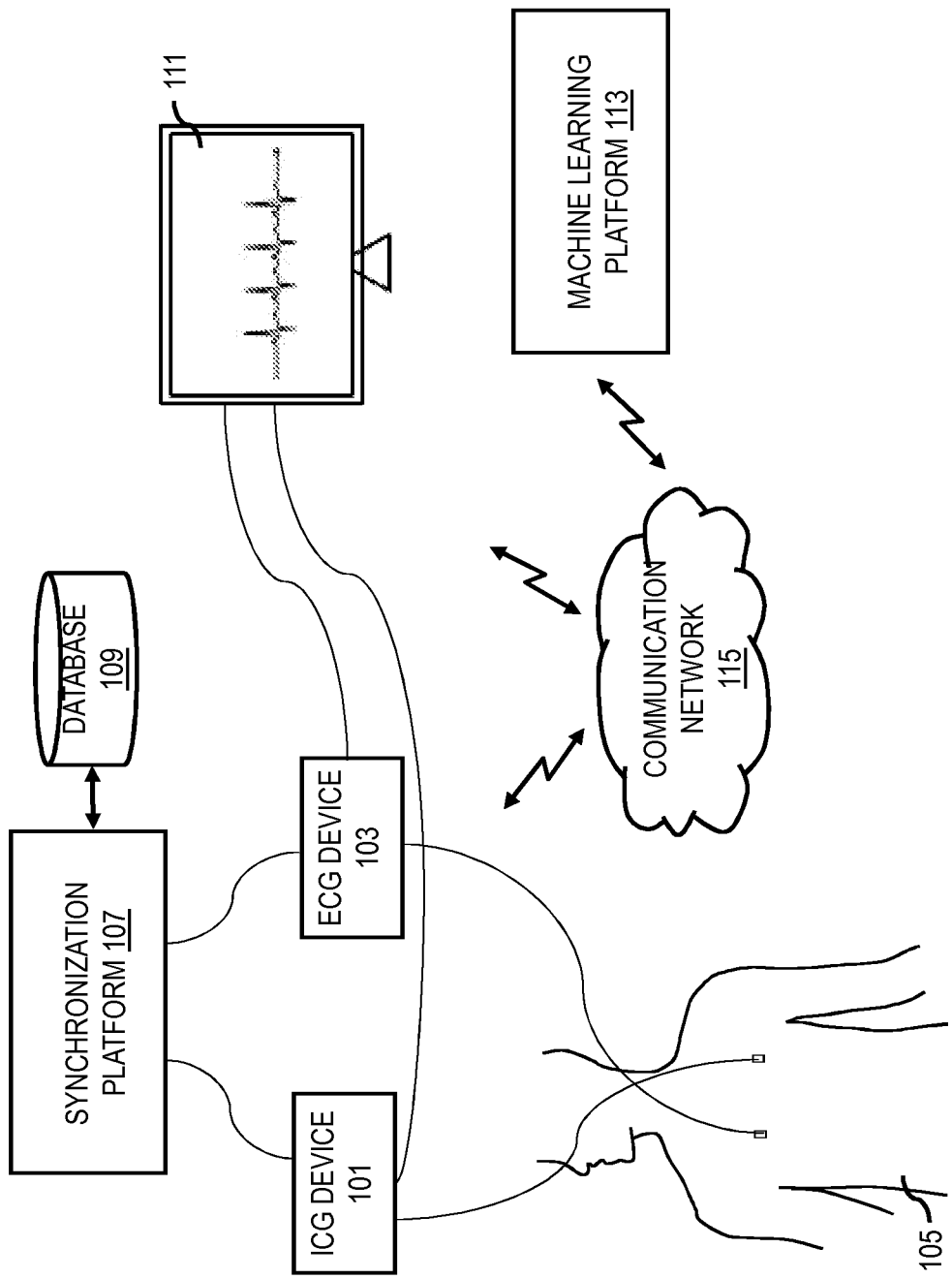
FIG. 1A is a diagram of a system capable of synchronizing an ICG measurement period with an ECG signal to reduce patient auxiliary current, according to one example embodiment.

FIG. 1 is a diagram of a system capable of synchronizing an ICG measurement period with an ECG signal to reduce patient auxiliary current, according to one example embodiment. Typically, an ICG device operates by placing electrodes at points of a patient's body that, e.g., delineate the thorax to measure various properties of the patient's heart. The ICG device then intentionally transmits or injects electrical current (e.g., high frequency, low magnitude current) through the thorax or chest of the patient via the electrodes. Measurements of variations in the impedance of the injected current as it travels through the thorax over time are then taken to characterize various properties of the heart. For example, impedance variations detectable by the ICG device can result from the volumetric expansion or contraction of the vascular system and chambers of the heart, and/or the alignment of bloods cells from changes in velocities during a cardiac cycle or hear beat. The patient auxiliary current is injected continuously for the duration of the measurement.

Historically, the signal-to-noise ratio of the ICG device is very sensitive to the patient auxiliary currents (e.g., the intentionally injected electrical currents to the body) used make a measurement. In other words, with respect to sensitivity of the ICG device, the higher the current that is injected, the better the resulting ICG signal. However, this push towards higher current is counterbalanced by the need to protect patient safety. For example, regulatory authorities or industry standards bodies can set safety limitations on how much current can be applied to a patient. One example of such a limitation is the International Electrotechnical Commision's ("IEC") general standard IEC 60601-1—Medical electrical equipment—Part 1: General requirements for basic safety and essential performance which specifies that the patient auxiliary current may not exceed 100 uA in normal condition, and to 500 uA of patient auxiliary current in a single fault condition, but not continuously. However, the standard of 100 uA of patient auxiliary current is very low when compared against many current ICG solutions which use over 1 mA currents and even up to 5 mA to achieve a desired level of performance. Accordingly, ICG device manufacturers face a significant technical problem of developing ICG devices and processes that can both comply with patient safety standards and provide a desired ICG signal quality.

To address this problem, system 100 of FIG. 1 introduces the capability to synchronize an ICG measurement period with an ECG signal to reduce patient auxiliary current. In one embodiment, the system 100 includes an ICG device 101 that reduces injected current by taking measurements only during periods of the cardiac cycle that are interesting or related to properties of interest indicated by a corresponding ECG signal measured by an ECG device 103 (as opposed to continuous measurements and current injection used in traditional ICG devices). In other words, the system 100 enables the ICG device 101 to inject a higher relative current (e.g., 1 mA) for a shorter duration (e.g., 100 ms) that is synchronized to an ECG signal or ECG feature within the ECG signal to result in effectively reducing the patient auxiliary current injected into the patient 105 during cardiac cycles or heartbeats during a measurement period. For example, the ECG device 103 can detect a beginning of an ECG feature for a heartbeat detected in a corresponding ECG signal, and then trigger the ICG device 101 to inject a current at a relatively high current (e.g., 1 mA) to measure an ICG signal for a short duration (e.g., 100 ms) as a opposed to the full duration of the heartbeat (e.g., 1 s for a heart beating at 60 beats per minute). Accordingly, the system 100 enables better ICG signal quality (e.g., resulting from the relatively higher current that can be applied) while complying with maximum current limits to protect patient safety. In one embodiment, the ECG device and the ICG device are a part of a single device. In one example embodiment, a single device may comprise a housing containing an ECG device and an ICG device as its components. This single device may measure both ECG and ICG signals of a patient.

Device manufacturers face further technical challenges when implementing ECG and ICG devices in wearable devices because available battery power is limited to provide greater portability and user comfort. Accordingly, reducing battery usage also is a high priority under this use case. For example, operating wearable ICG devices in a traditional continuous mode for extended periods of time can cause significant battery drain because current is continuously drawn from the batteries to make ICG measurements. Under the various embodiments described herein, synchronized ICG measurements draw current for injection for only a portion of the full cardiac cycle (e.g., 100 ms out of a is cycle), thereby reducing battery consumption and increasing battery run-time.

In one embodiment, it is contemplated that ECG feature refers to any portion or deflection of a signal generated or used by the ECG device 103. For example, an ECG feature may correspond to any of the traditionally labeled deflections in an ECG signal generally represented by the letters P, Q, R, S, and T. In addition, the ECG feature can be a manmade signal generated by the ECG device 103 itself such as a pace signal. In one embodiment, the system 100 is configured to determine an interesting portion of the cardiac cycle based on the ECG features to initiate measuring of the ICG signal.

Figure 1B:
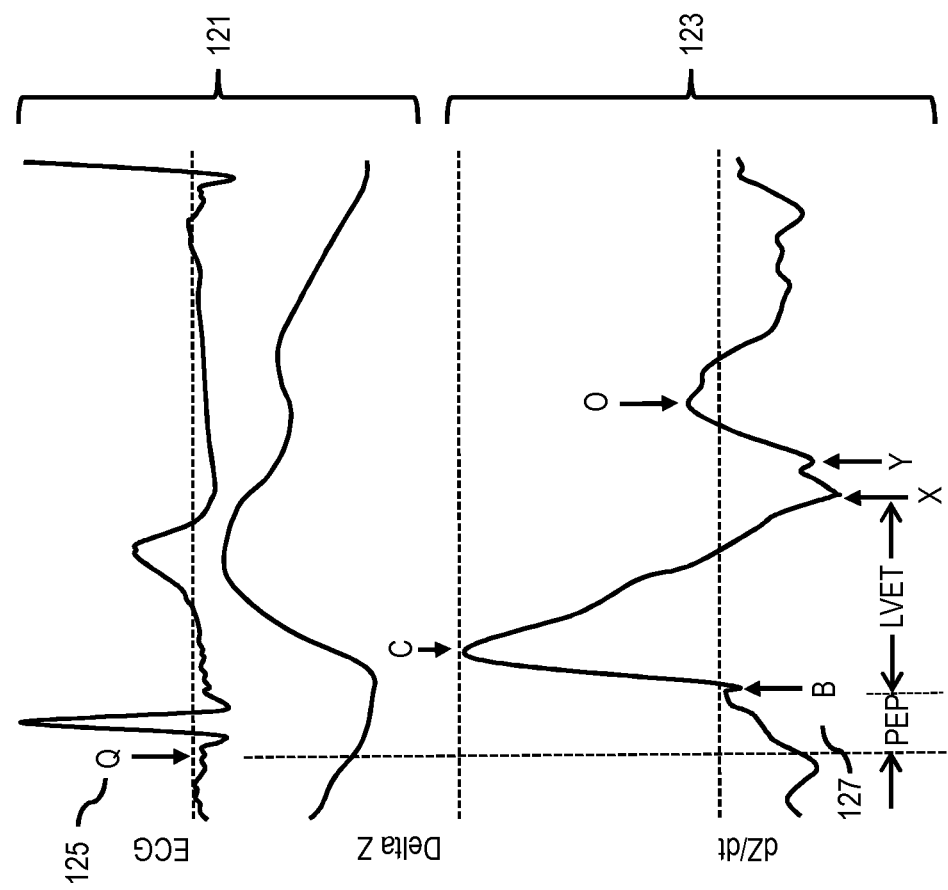
FIG. 1B is a diagram of simultaneously measured ECG and ICG signals, according to one embodiment.

FIG. 1B is a diagram of simultaneously measured ECG and ICG signals, according to one embodiment, and illustrates the relationship between the ECG features of ECG signal 121 and the measurement periods of interest in the ICG signal 123. For example, it is known that feature 125 corresponding to the Q-wave of the ECG signal 121 and the corresponding B-point 127 of the ICG signal 123 can be used to measure the pre-ejection period ("PEP") of the heart. This PEP period is interesting because it is a systolic time interval that can be used in conjunction with the photoplethysmography (PPG) signal, for example, measured from the radial artery (from the place in arm where you can feel the pulse). Having the ECG and ICG signals, the pulse transit time (PTT) can be estimated more accurately than just using the PPG and ECG. Actually, ECG+PPG gives the pulse arrival time (PAT) instead of the PTT. Although PAT would be easier to measure it is known to correlate worse to blood pressure than PTT. Thus, adding ICG to the ECG+PPG measurement system would enable better non-invasive blood pressure ("NIBP") measurement. In one embodiment, PEP also reflects the contractility of the heart muscle. PEP and VET can be used separately from PAT applications in heart monitoring.

In one embodiment, the PEP itself and PEP variability would be valuable parameters to be measured in any system. For example, PEP variability could give information about our stress levels along with the heart rate variability (HRV). HRV reflects especially the parasympathetic part of the stress regulation and PEP variability is a promising indicator of the sympathetic part of the stress regulation. Accordingly, the B-point 127 can be an interesting feature to measure with the ICG device 101. It is noted that the B-point 127 is provided as just one example of an interesting portion of the ICG signal that can be measured using the various embodiments described herein. It is contemplated that any portion of the ICG signal can be correlated with a corresponding ECG signal (e.g., an ECG signal collected simultaneously with the ICG signal).

In one example use case where the triggering ECG feature is a pace signal, the system 100 can measure an ECG signal and find the pace of that signal. For example, as discussed above, the pace can be determined from the pace signal transmitted by some ECG devices 103 (e.g., because of their usage as pace makers in some cases). When the heart pace or other ECG feature characteristic is known, the system 100 can start and/or stop ICG measurements and, correspondingly the current injections for ICG measurements, in synchronization with the ECG. In one embodiment, the synchronization process can be implemented into an integrated chip ("IC") or be microcontroller controlled. In one embodiment, the IC and/or the microcontroller comprises the synchronization platform 107.

In one embodiment, the system 100 initiates measurement of an ICG signal upon detecting an ECG feature (e.g., start of the Q wave). In another embodiment, the system 100 stops measurement of an ICG signal after a predetermined period of time or upon detecting another ECG feature (e.g., end of the of QRS complex) subsequent to the initial ECG feature (e.g., the Q wave) that triggered the measurement. In one embodiment, the system 100 initiates measurement of the ICG signal by injecting a relatively high current to improve signal quality (e.g., a high 1 mA peak current) in synchronization with the detected ECG features. For example, in one embodiment, detecting a Q-wave in the ECG signal can trigger the initiating of the ICG measurement so that the ICG measurement can capture the B-point 127 which is of interest for the various reasons discussed above. In this example, the system 100 measures the ICG signal from the detected start of the Q wave for a predetermined period of time (e.g., 100 ms) that is estimated to encompass the cardiac PEP for a typical patient. The B-point 127 is an interesting feature of ICG signal that comes after the QRS complex of the ECG signal, hence the measurement of an ICG signal can be very short. In one example embodiment, system 100 may schedule the measurement period for an ICG signal only during 100 millisecond (ms) time interval between the heart beats. If the heart rate is 60 Beats per Minute (BPM) then the duty cycle of the ICG signal is only 10% for the heart rate of 60 bpm. Therefore, the root mean square (RMS) of the ICG calculated over the predetermined period is significantly reduced. For example, the 1 mA peak current injected during the measurement period is effectively reduced to approximately 320 uA RMS, thereby achieving the advantageous result of reducing the patient 105's overall auxiliary current exposure.

In one embodiment, the system 100 can further enhance patient safety by configuring the ICG device 101 to avoid injecting current at points in the cardiac cycle that are most affected by patient auxiliary current. For example, the period of ventricular repolarization reflected by the T-wave in an ECG signal is particularly vulnerable to patient auxiliary current. Typically, the T-wave comes roughly 100 ms after the S-wave of the ECG signal. It is known that the heart is vulnerable to patient auxiliary current when the T-wave begins because external current may cause arrhythmia during this time period. Therefore, the system 100 can be configured to stop or avoid injecting any current during the T wave further advantageously improve patient safety. In one embodiment, the system 100 can also be configured to observe the current limitation during the T-wave while applying relatively higher currents during other periods of the cardiac cycle.

As shown in FIG. 1, the system 100 comprises the ICG device 101 and the ECG device 103 having connectivity to a synchronization platform 107. In one embodiment, synchronization platform 107 performs the various embodiments of the process for synchronizing ICG measurement with the detected features of an ECG signal. The ICG and ECG signals and related data may be stored in database 109 and/or presented on a display device 111. In one embodiment, the display device 111 may include any type of device for presenting visual information such as, for example, a computer monitor or flat-screen display. In another scenario, the display device 111 may be equipped with user input devices, such as buttons or touch screen capabilities for enabling user input, operation and control of the system. Although depicted as separate components, in one embodiment, the ICG device 101, the ECG device 103, the synchronization platform 107, the database 109, and/or the display 111 may be implemented in a one device or a set of integrated components.

In one embodiment, the synchronization platform 107 has connectivity to a machine learning platform 113 over the communication network 115 to set parameters for duty time (e.g., ICG measurement start time, stop time, and/or duration) and/or current injection settings (e.g., level of injection current) of the system 100. In one embodiment, the machine learning platform 113 may implement machine learning to reduce the duty time and the total average current. In one scenario, the machine learning platform 113 may train a machine learning system with recorded ECG data and ICG data from multiple patients. Then, a per-person optimized current and a measurement period is determined by observing different features statistically typical for certain group of patients. In one scenario, in an offline machine learning setting the machine learning platform 113 may collect an ECG data and an ICG data beforehand, and a model is fitted with the collected data. On the other hand, in an online machine learning setting, the machine learning platform 113 may refine the model by exploring new settings with the current patients. In one embodiment, in an offline machine learning setting continuous ECG data and ICG data is collected from multiple patients (including patients with heart conditions) for determining the measurement periods in order to reduce the total duty cycle time. Then, the machine learning platform 113 detects a B-point on the continuous data to compute a ground truth B-point. Next, the machine learning system is trained to propose an optimal measurement periods given a duty cycle budget. With a validation data, the machine learning system can be measured in terms of how much error is being increased by reducing the total duty cycle. In one embodiment, any combination of hardware and software can run the training and/or inference algorithms based on recorded ECG and ICG data. In another embodiment, the machine learning platform 113 may be embedded within a device hence access to the communication network 115 is not necessitated to set parameters for ICG measurement duration and/or level of injection current.

In another embodiment, the machine learning platform 113 may implement reinforcement learning for determining an optimal current and measurement periods in order to reduce total average current. In one scenario, different patients have different response to ICG treatments. For some patients, a smaller current may be utilized, which could also enable using longer measurement periods or reduce the total average current. This method utilizes online reinforcement learning (initialized from existing recordings) to adjust the current and measurement periods to be optimal for the current patient. In a further embodiment, random or semi-random measurement periods may be implemented to collect data for the machine learning systems in a battery-saving and current-friendly fashion.

In one embodiment, an ECG device 103 measures electrical activity of the heart and therefore provides useful information concerning the sequence and pattern of muscular activity of the heart chambers. In one scenario, ECG device 103 includes electrodes that are placed on a patient in specific location to detect electrical impulses generated by the heart during each beat. The electrodes usually consist of a conducting gel embedded in an electro-conductive material, to which cables are clipped on. Each lead, or output from a pair of electrodes, records the electrical activity resulting from a depolarization and a repolarization of the heart. In another scenario, the ECG device 103 also detects manmade signals, for example, signals from implanted pacemakers (herein after "pace.") The pace signal is relatively short, for example, tens of microseconds to a couple of milliseconds, with an amplitude ranging from a few millivolts to nearly a volt. Often, the ECG device 103 detects the presence of a pace signal while simultaneously preventing it from distorting the signals from the heart. In one scenario, these electrical signals are transferred by the electrodes to a stationary ECG monitor (e.g., display device 111).

An ECG device 103 comprises of an analog front-end (AFE). The primary function of the AFE is to digitize the heart signals. This process is complicated by the need to reject interference from other signals (e.g., strong RF sources, pace signals, lead-off signals, common-mode line frequency, signals from other muscles, and electrical noise). In one scenario, the AFE detects pace signals, lead-off detections, respiration rate, and patient impedance. All of this is done on several channels simultaneously or near simultaneously. In one scenario, digitizing the pace signal allows pace analysis that reduces the number of false pace indications and may even detect faults in the pacemaker or its connections. In one embodiment, the measurement requirements of an ECG can be met by using the brute force of powerful analog-to-digital (ADC) to simultaneously digitize the signals on all nine electrodes to a noise-free resolution of about 20 bits at a rate of 200 ksps, although any other resolution and bitrate can be used. A digital signal processor (DSP) can then be used to calculate the signal for each lead, isolate the pace signal, isolate the lead-off/respiration signals, and filter out unwanted frequencies. In one scenario, any signal denoising algorithm, including one using machine learning from at least one of the signals, can be utilized in combination of this invention.

In one embodiment, the ICG device 101 produces ICG signals from monitoring movement and volume of blood as a result of mechanical movements of the heart (e.g., the heart contracting). As previously discussed, ICG device 101 includes electrodes that are placed over a patient's body. Then, an electric current (high frequency, low magnitude) is transmitted to the patient across outer electrodes positioned, for example, on the patient's head and lower thorax. Subsequently, the voltage differences between sensing inner electrodes positioned between the outer electrodes on the patient's neck and chest are measured and used to compute an impedance.

By way of example, the communication network 115 of system 100 includes one or more networks such as a data network, a wireless network, a telephony network, or any combination thereof. It is contemplated that the data network may be any local area network (LAN), metropolitan area network (MAN), wide area network (WAN), a public data network (e.g., the Internet), short range wireless network, or any other suitable packet-switched network, such as a commercially owned, proprietary packet-switched network, e.g., a proprietary cable or fiber-optic network, and the like, or any combination thereof. In addition, the wireless network may be, for example, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., worldwide interoperability for microwave access (WiMAX), Long Term Evolution (LTE) networks, code division multiple access (CDMA), wideband code division multiple access (WCDMA), wireless fidelity (WiFi), wireless LAN (WLAN), Bluetooth®, Internet Protocol (IP) data casting, satellite, mobile ad-hoc network (MANET), and the like, or any combination thereof.

By way of example, the ICG device 101, the ECG device 103, and the synchronization platform 107 communicate with each other and other components of the communication network 115 using well known, new or still developing protocols. In this context, a protocol includes a set of rules defining how the network nodes within the communication network 115 interact with each other based on information sent over the communication links. The protocols are effective at different layers of operation within each node, from generating and receiving physical signals of various types, to selecting a link for transferring those signals, to the format of information indicated by those signals, to identifying which software application executing on a computer system sends or receives the information. The conceptually different layers of protocols for exchanging information over a network are described in the Open Systems Interconnection (OSI) Reference Model.

Communications between the network nodes are typically effected by exchanging discrete packets of data. Each packet typically comprises (1) header information associated with a particular protocol, and (2) payload information that follows the header information and contains information that may be processed independently of that particular protocol. In some protocols, the packet includes (3) trailer information following the payload and indicating the end of the payload information. The header includes information such as the source of the packet, its destination, the length of the payload, and other properties used by the protocol. Often, the data in the payload for the particular protocol includes a header and payload for a different protocol associated with a different, higher layer of the OSI Reference Model. The header for a particular protocol typically indicates a type for the next protocol contained in its payload. The higher layer protocol is said to be encapsulated in the lower layer protocol. The headers included in a packet traversing multiple heterogeneous networks, such as the Internet, typically include a physical (layer 1) header, a data-link (layer 2) header, an internetwork (layer 3) header and a transport (layer 4) header, and various application (layer 5, layer 6 and layer 7) headers as defined by the OSI Reference Model.

Figure 2:
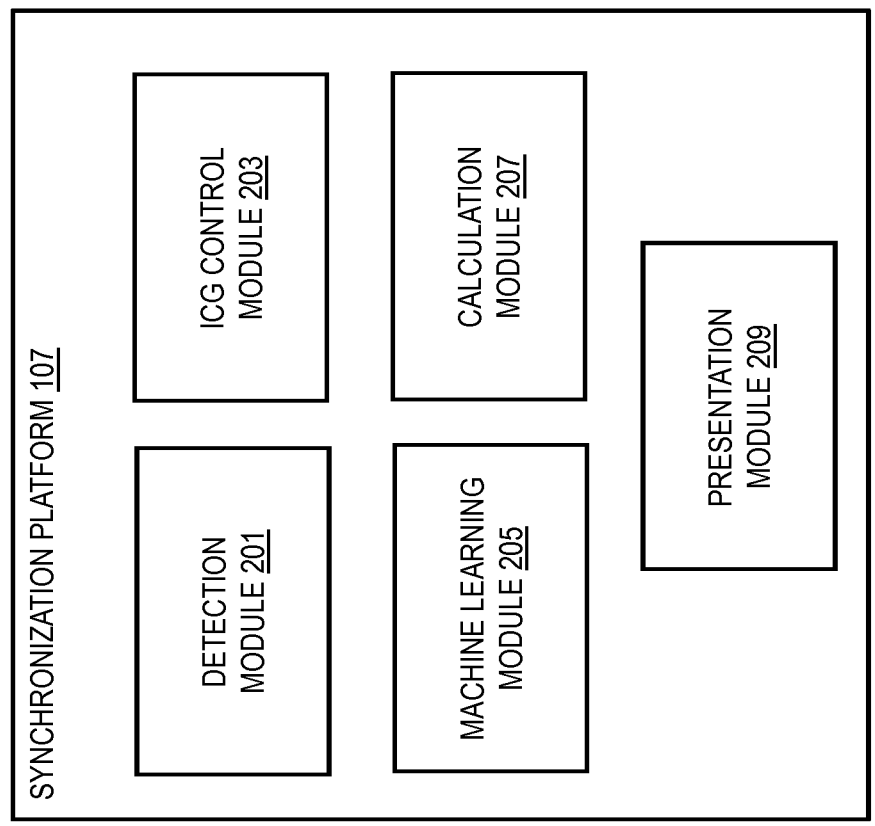
FIG. 2 is a diagram of the components of the synchronization platform 107, according to one example embodiment.

FIG. 2 is a diagram of the components of the synchronization platform 107, according to one example embodiment. By way of example, the synchronization platform 107 includes one or more components for synchronizing an ICG measurement period with an ECG signal to reduce patient auxiliary current during diagnosis of heart conditions using electrical medical devices. It is contemplated that the functions of these components may be combined in one or more components or performed by other components of equivalent functionality. In one embodiment, the synchronization platform 107 comprises one or more detection modules 201, ICG control modules 203, machine learning modules 205, calculation modules 207 and presentation modules 209, or any combination thereof.

In one embodiment, the detection module 201 signals an ECG device 103 to begin measuring ECG signals of a patient simultaneously or at least substantially simultaneously (e.g., initiating the collection of both ECG and ICG signals within a time threshold that is designated as simultaneous). In one embodiment, the detection module 201 initiates the two devices by placing the ECG device 103 into an active measurement mode where it is collecting data while placing the ICG device 101 in a ready state but not actively injecting current to make ICG measurements as an initial state. The detection module 201 begins collecting and processing the ECG signals received from the ECG device 103 to detect one or more ECG features. As discussed above, the ECG features can be any of the traditional deflections observed in a typical ECG signal (e.g., P, Q, R, S, and T). In one embodiment, the detection module 201 is configured to detect specific ECG features (e.g., a QRS complex, an S wave, or a beginning of a T wave) that have been correlated with portions of an ICG signal that are known to be of interest (e.g., a B-point, PEP, etc.).

In one embodiment, after detecting an ECG feature of interest, the detection module 201 signals the detection to the ICG control module 203 to synchronizes a start and/or a stop of a measurement of an ICG signal based on one or more ECG features. In one embodiment, the ICG control module 203 is configured to trigger the beginning of the ICG measurement by an ICG device 101 to coincide with the detection of the ECG feature for a predetermined period of time. By way of example, the predetermined period of time may be set to 100 ms so that the measurement period covers the duration of the QRS complex of the ECG which corresponds to the PEP in the ICG signal which ends with the B-point of the ICG signal. The 100 ms measurement is a default value intended to cover a majority of the patient population. However, the upper limit of the normal reference values is 124 ms in males and 118 ms in females.

Accordingly, under this circumstance, the ICG control module 203 can be configured to increase the measurement period so that a B-point is detected. In one embodiment, the ICG control module 203 can increase the measurement period by predetermined amounts of time (e.g., 5 ms increments) until the B-point is detected in the ICG signal. Alternatively, the ICG control module 203 may engage the machine learning module 205 to make further refinements to the measurement period. In one example use case, the ICG control module 203 synchronizes a start of an ICG signal measurement based on a detected start of the Q wave in an ECG signal to estimate a cardiac PEP. As noted above, the cardiac PEP occurs between the Q wave in the ECG signal and the B-point in the ICG signal.

In one embodiment, the ICG control module 203 does not use a predetermined measurement period. Instead, the ICG control module 203 can be configured to end the measurement period by detecting a subsequent ICG feature. For example, the ICG control module 203 can be configured to start an ICG measurement when the start of the Q wave is detected and then end the measurement of when end of the S wave is detected by the detection module 201. In this way, the entirety of the QRS is covered for all patients regardless of the variabilities in the durations of the QRS complex for individual patients. This method also advantageously avoids having an unnecessarily long predetermined measurement period if a patient's QRS complex is less than the default period of 100 ms, thereby further reduction patient auxiliary current.

In yet another embodiment, the ICG control module 203 is configured to avoid measurements or to perform measurements with reduced current (e.g., below specified current limits) based on certain detected ECG features. For example, as discussed above, the T-wave of an ECG signal represents a particularly vulnerable period where the heart is more susceptible to irregularities caused by external current. Accordingly, the ICG control module 203 can avoid imitating ICG measurements during the T-wave of the ECG signal to further enhance patient safety.

In one embodiment, the machine learning module 205 alone or in combination with the machine learning platform 113 calculates an optimized duty cycle (e.g., ICG measurement period) and/or an optimized current level to be administered to at least one patient. In one embodiment, the optimized duty cycle and/or current level can be determined for a population of patients, for individual classes of patients (e.g., based on demographics, health status—e.g., healthy or sick, etc.), and/or for individual patients (e.g., historical data and/or reinforcement learning). By way of example, the machine learning process involves determining a ground truth for a feature of interest in the ICG signal using, e.g., a continuous ICG measurement (e.g., an ICG measurement which spans the entire cardiac cycle). For example, if the B-point (e.g., which indicates the end of the cardiac PEP) is the feature of interest in the ICG signal, the B-point can be detected in the continuous ICG data for the patients. The period for the start of the PEP to the ground truth B-point can be measured, with the period representing the optimized duty cycle. Similarly, current levels can be varied to find an optimized current level that provides sufficient signal quality (e.g., based on signal to noise ratio or any other measure of signal quality) that can still detect the feature of interest in the ICG signal based on the ground truth. In this case, a ground truth detection of the ICG feature of interest (e.g., the B-point) can be made at a higher current, and then subsequently lower currents can be measured in specific individual to determine the lowest current that can detect the feature as the optimized current.

More specifically, a measurement period for an ICG signal, or a combination thereof based, at least in part, on observation of an ECG feature and/or ICG feature statistically standard for a particular group of patients. In one scenario, the calculation module 207 collects an ECG data and an ICG data for a particular group of patients on a continuous basis. Then, the calculation module 207 assesses any new ECG feature and/or ICG feature associated with the particular group of patients. Subsequently, the calculation module 207 refines the stored ECG data and the ICG data. In one example embodiment, the calculation module 207 detects at least one ICG feature (e.g., B-point) for a particular group of patients. Then, the calculation module 207 computes a ground truth B-point to determine an optimal measurement period for an ICG signal. In another embodiment, the calculation module 207 calculates an optimized current administered to at least one patient, a measurement period for an ICG signal, or a combination thereof based, at least in part, on observation of an ECG feature and/or ICG feature statistically standard for at least one patient. In one example embodiment, the calculation module 207 causes an adjustment in the total average current and the measurement period, for example, smaller current is utilized activating a longer measurement periods, and a higher current is utilized activating a shorter measurement periods.

In one embodiment, the presentation module 209 obtains information and/or updates from the other modules, e.g., from the detection module 201. Then, the presentation module 209 continues with generating a graphical representation of the ECG signal, the ICG signal, or a combination thereof in at least one device.

The above presented modules and components of the synchronization platform 107 can be implemented in hardware, firmware, software, or a combination thereof. Though depicted as a separate entity in FIG. 1, it is contemplated that the synchronization platform 107 may be implemented for direct operation by respective ICG device 101 and/or ECG device 103. As such, the synchronization platform 107 may generate direct signal inputs by way of the operating system of the ICG device 101 and/or ECG device 103 for interacting with various applications. In another embodiment, one or more of the modules 201-209 may be implemented for operation by respective UEs, as the synchronization platform 107, or combination thereof. Still further, the synchronization platform 107 may be integrated for direct operation with other services, such as in the form of a widget or applet, in accordance with an information and/or subscriber sharing arrangement. The various executions presented herein contemplate any and all arrangements and models.

Figure 3:
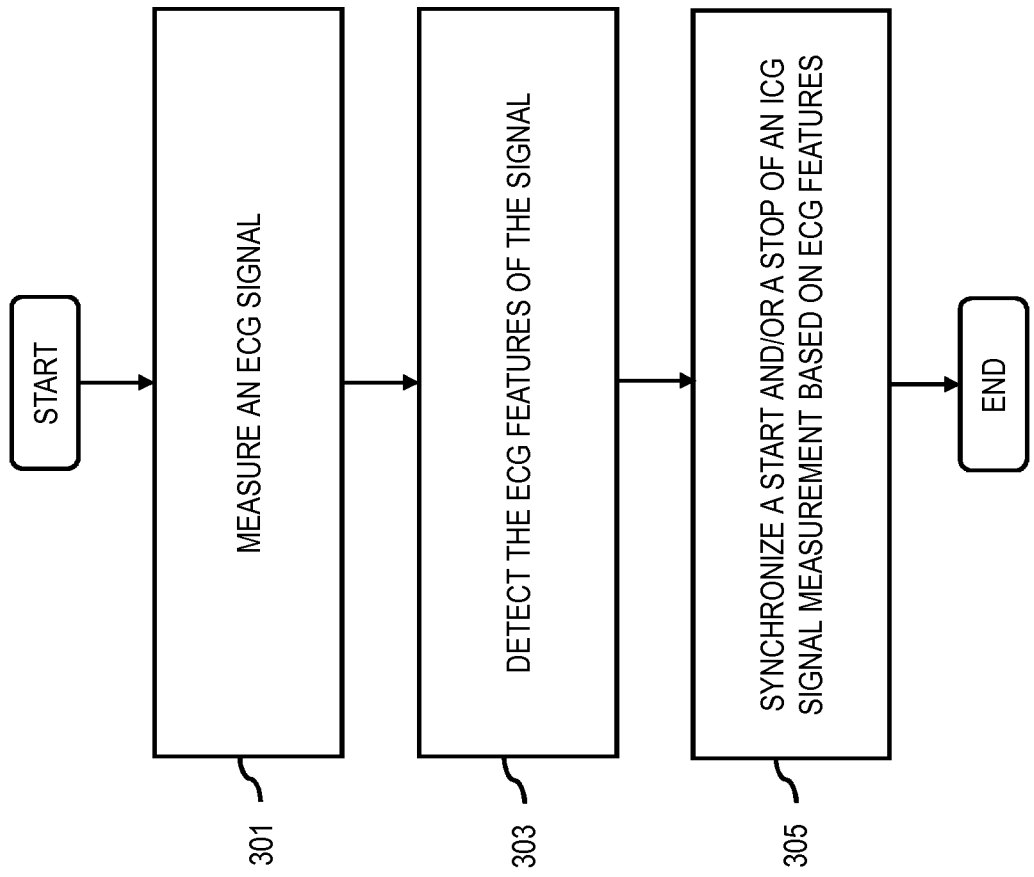
FIG. 3 is a flowchart of a process for synchronizing an ICG measurement period with an ECG signal to reduce patient auxiliary current, according to one example embodiment.
Figure 12:
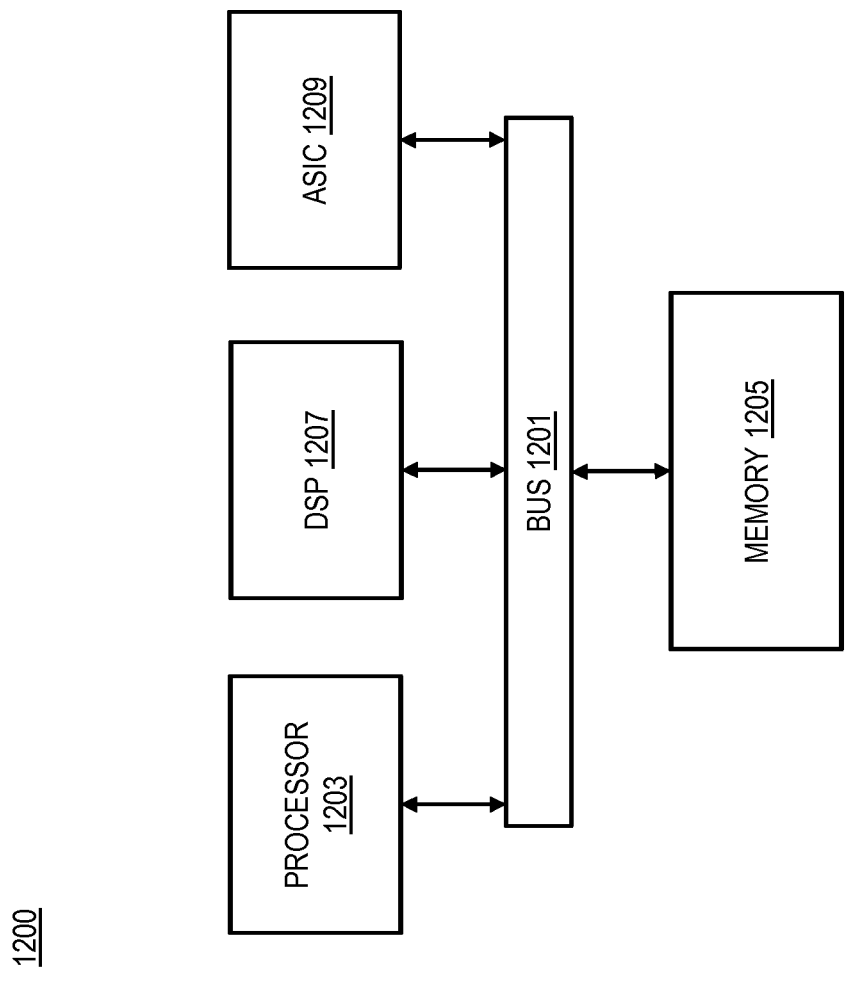
FIG. 12 is a diagram of a chip set that can be used to implement an embodiment of the invention.

FIG. 3 is a flowchart of a process for synchronizing an ICG measurement period with an ECG signal to reduce patient auxiliary current, according to one example embodiment. In one embodiment, the synchronization platform 107 performs the process 300 and is implemented in, for instance, a chip set including a processor and a memory as shown in FIG. 12.

In step 301, the synchronization platform 107 measures an ECG signal of a patient via an ECG device. In one scenario, an ECG feature refers to any portion or deflection of a signal generated or used by the ECG device 103. For example, an ECG feature may correspond to any of the traditionally labeled deflections in an ECG signal generally represented by the letters P, Q, R, S, and T. In addition, the ECG feature can be a manmade signal generated by the ECG device 103 itself such as a pace signal. In one embodiment, the system 100 is configured to determine an interesting portion of the cardiac cycle based on the ECG features to initiate measuring of the ICG signal. In one embodiment, the ECG device 103 can detect a beginning of an ECG feature for a heartbeat detected in a corresponding ECG signal to trigger the ICG device 101 to inject a current. In one embodiment, the ECG device and the ICG device are a part of a single device. In one example embodiment, a single device may comprise a housing containing an ECG device and an ICG device as its components. This single device can measure both ECG and ICG signals of a patient.

In step 303, the synchronization platform 107 processes the ECG signal to cause, at least in part, a detection of one or more ECG features of the signal. In one embodiment, the one or more ECG features of the ECG signal includes a P wave, a Q wave, an R wave, an S wave, and a T wave. In one scenario, the synchronization platform 107 may process the ECG signal to find at least one feature within the ECG signal (e.g., a QRS complex, an S wave, a T wave) and based on the detected feature the synchronization platform 107 may trigger the current for an ICG reading or stop the current for an ICG reading. In another embodiment, the one or more ECG features is a pace signal of the ECG device. In one scenario, the ECG device detects signals from implanted pacemakers (e.g., some ECG AFEs can give the pace because of their usage in pacemakers) to measure the effects such devices used to regulate the heart. In one scenario, an ECG device must detect the presence and effects of pacemakers when patients with implanted pacemakers undergo ECG testing. It is important to be able to detect and identify pacing artifacts because they indicate the presence of a pacemaker and help in evaluating its interaction with the heart. In one embodiment, the start and/or the stop of the measurement of an ICG signal is synchronized to the detected pace signal.

In step 305, the synchronization platform 107 synchronizes a start, a stop, or a combination thereof of a measurement of an ICG signal of the patient via an ICG device based, at least in part, on the detection of the one or more ECG features. In one scenario, the synchronization platform 107 reduces a patient auxiliary current by controlling the start and the stop of the measurement period of an ICG signal in synchronization with an ECG features. In one embodiment, the synchronization platform 107 stops an ICG measurement after estimating a cardiac PEP. In one scenario, the cardiac PEP occurs between a Q wave of the QRS complex and the B-point in the ICG signal. In another embodiment, the synchronization platform 107 discontinues injecting an electric current upon inception of the T wave because the heart is vulnerable to patient auxiliary current when the T-wave begins because external current may cause arrhythmia during this time period. In one scenario, the T wave follows the S wave of the QRS complex, and the synchronization platform 107 stops or avoids injecting any current during the T wave, thereby improving patient safety.

Figure 4:
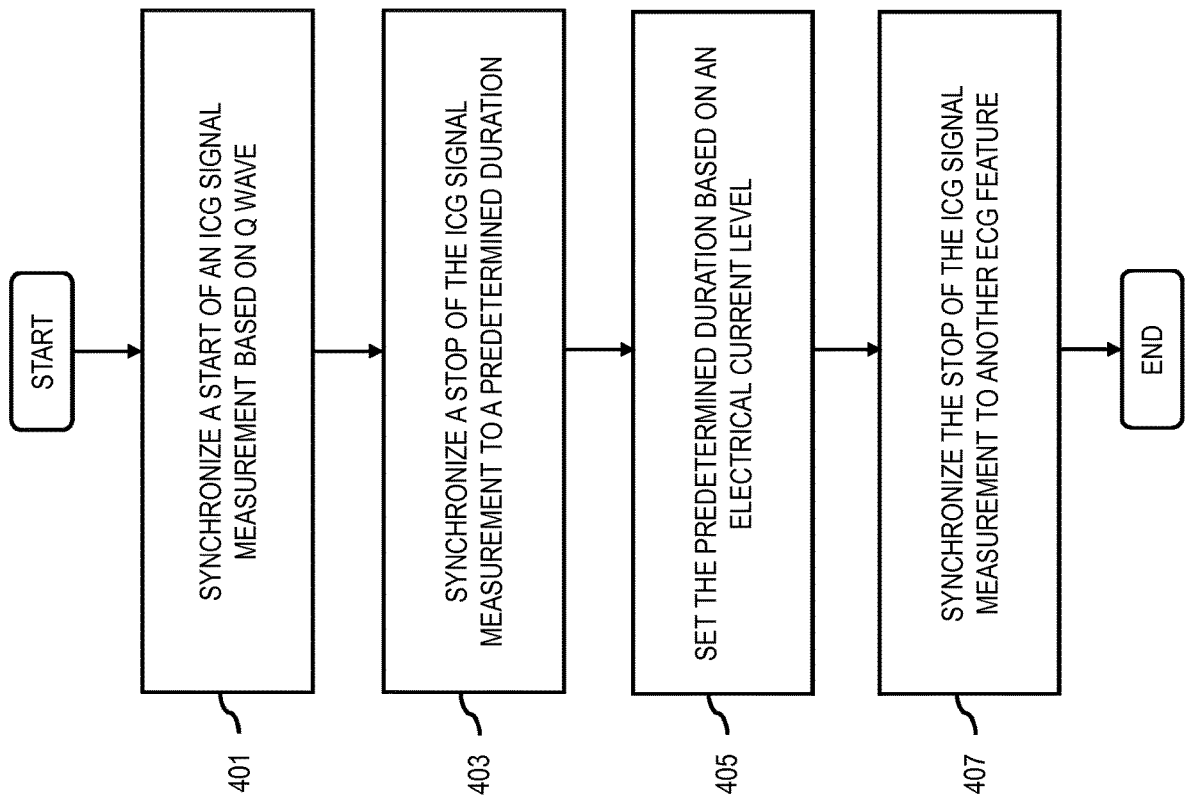
FIG. 4 is a flowchart of a process for synchronizing the start and/or the stop of an ICG signal measurement, according to one example embodiment.

FIG. 4 is a flowchart of a process for synchronizing the start and/or the stop of an ICG signal measurement, according to one example embodiment. In one embodiment, the synchronization platform 107 performs the process 400 and is implemented in, for instance, a chip set including a processor and a memory as shown in FIG. 12.

In step 401, the synchronization platform 107 synchronizes the start of the measurement of the ICG signal based on a detected start of an ECG feature (i.e., Q wave). In one scenario, the synchronization platform 107 triggers initiation of the ICG measurement based on detection of a Q-wave in the ECG. The measurement of ICG signal from the detected start of the Q wave for a predetermined period of time captures the B-point and is estimated to encompass the cardiac PEP for a typical patient. In one scenario, the predetermined period of time may be a set time period that covers the duration of the QRS complex of the ECG which corresponds to the PEP in the ICG signal which ends with the B-point of the ICG signal. In one example embodiment, the predetermined period of time may be set to 100 ms (a default value intended to cover a majority of the patient population).

In step 403, the synchronization platform 107 synchronizes the stop of the measurement of the ICG signal to a predetermined duration following the start of the measurement of the ICG signal. In one embodiment, the synchronization platform 107 stops measurement of an ICG signal upon detecting another ECG feature (e.g., end of the of QRS complex) subsequent to the initial ECG feature (e.g., the Q wave) that triggered the measurement. In one example embodiment, the synchronization platform 107 stops the measurement of an ICG signal upon determination of the cardiac PEP. In one scenario, the cardiac PEP occurs between a Q wave of the QRS complex and the B-point in the ICG signal.

In step 405, the synchronization platform 107 sets the predetermined duration based on an electrical current level injected into the patient during the measurement of the ICG signal. In one embodiment, the current levels can be varied to find an optimized current level that provides sufficient signal quality (e.g., based on signal to noise ratio or any other measure of signal quality) that can still detect the feature of interest in the ICG signal based on the ground truth. In one scenario, a ground truth detection of the ICG feature of interest (e.g., the B-point) can be made at a higher current, and then subsequently lower currents can be measured in specific individual to determine the lowest current that can detect the feature as the optimized current. In one example embodiment, an auxiliary current (e.g., a high 1 mA peak current) may be applied by an ICG device for a predetermined duration of 100 ms so that the measurement period covers the duration of the QRS complex of the ECG which corresponds to the PEP in the ICG signal which ends with the B-point of the ICG signal. The 100 ms measurement is a default value intended to cover a majority of the patient population. However, the QRS complex for approximately 2% of the population can last for longer than 100 ms. Under this scenario, the resulting ICG measurement would only partially cover PEP and would not likely include the B-point, thus providing incomplete ICG data. Accordingly, the measurement period is increased by predetermined amounts of time (e.g., 5 ms increments) until the B-point is detected in the ICG signal.

In step 407, the synchronization platform 107 synchronizes the stop of the measurement of the ICG signal to another ECG feature detected subsequent to the Q wave. In one embodiment, another ECG feature includes, at least in part, an end of a QRS complex, an S wave, or a beginning of a T wave. In one embodiment, the synchronization platform 107 discontinues injection of any auxiliary current when end of the S wave is detected. In this way, the entirety of the QRS is covered for all patients regardless of the variabilities in the durations of the QRS complex for individual patients. In another embodiment, the synchronization platform 107 discontinues injection of any auxiliary current upon detecting inception of a T wave, thereby reducing the average current and improving patient safety.

Figure 5:
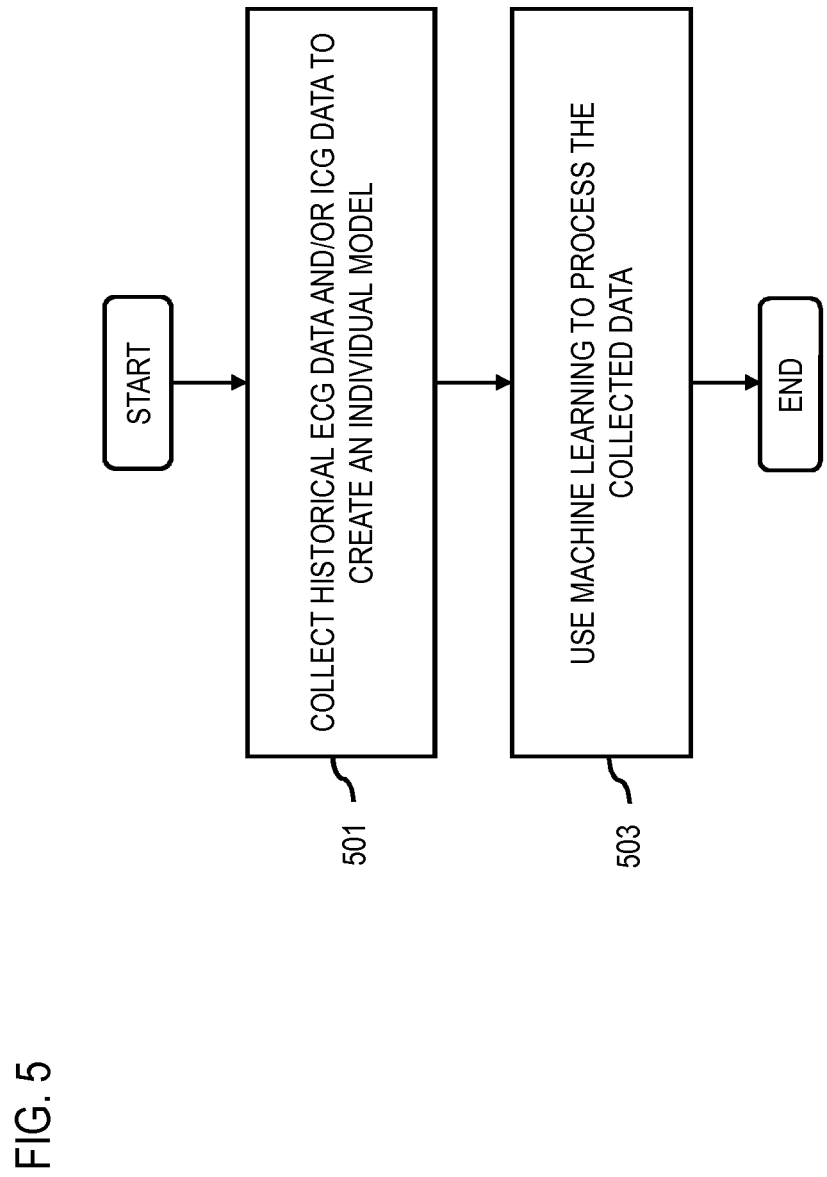
FIG. 5 is a flowchart of a process for processing historical ECG and ICG data for a patient using a machine learning process to set a predetermined duration and/or an electrical current level during an ICG signal measurement, according to one example embodiment.

FIG. 5 is a flowchart of a process for processing historical ECG and ICG data for a patient using a machine learning process to set a predetermined duration and/or an electrical current level during an ICG signal measurement, according to one example embodiment. In one embodiment, the synchronization platform 107 performs the process 500 and is implemented in, for instance, a chip set including a processor and a memory as shown in FIG. 12.

In step 501, the synchronization platform 107 collects historical ECG and ICG data for the patient to create an individual model. In one scenario, different patients have different response to ECG and ICG treatments. For some patients, a smaller current may be utilized, which could also enable using longer measurement periods or reduce the total average current. The synchronization platform 107 collects ECG data and ICG data for individual patients to determine a best electrical current level and timing for individual users. In one embodiment, the optimized duty cycle and/or current level can be determined for individual patients (e.g., historical data and/or reinforcement learning).

In step 503, the synchronization platform 107 processes the historical ECG data and the historical ICG data using a machine learning process to set a predetermined duration of the measurement of the ICG signal, an electrical current level to inject into the patient during the measurement of the ICG signal, or a combination thereof based on the individual model. In one scenario, the synchronization platform 107 utilizes a reinforcement learning (initialized from existing recordings) to adjust the electrical current and the measurement periods for an ICG signal to be optimal for the existing patients. In one scenario, a smaller current is utilized activating a longer measurement periods or a higher current is utilized activating a shorter measurement periods. In one example embodiment, the synchronization platform 107 may create an individual model for assessing different reactions of individual users to ECG and ICG treatments during different types of external stresses (e.g., exercises, mental stress, etc.). In another example embodiment, if a user in undergoing endurance training, the individual model may measure the strengthening of the heart, thereby letting the user know that his/her heart is functioning better with the improved fitness. In another scenario, the individual model may measure stiffening of a heart to reveal that a user has a disease and his/her heart function is declining.

Figure 6:
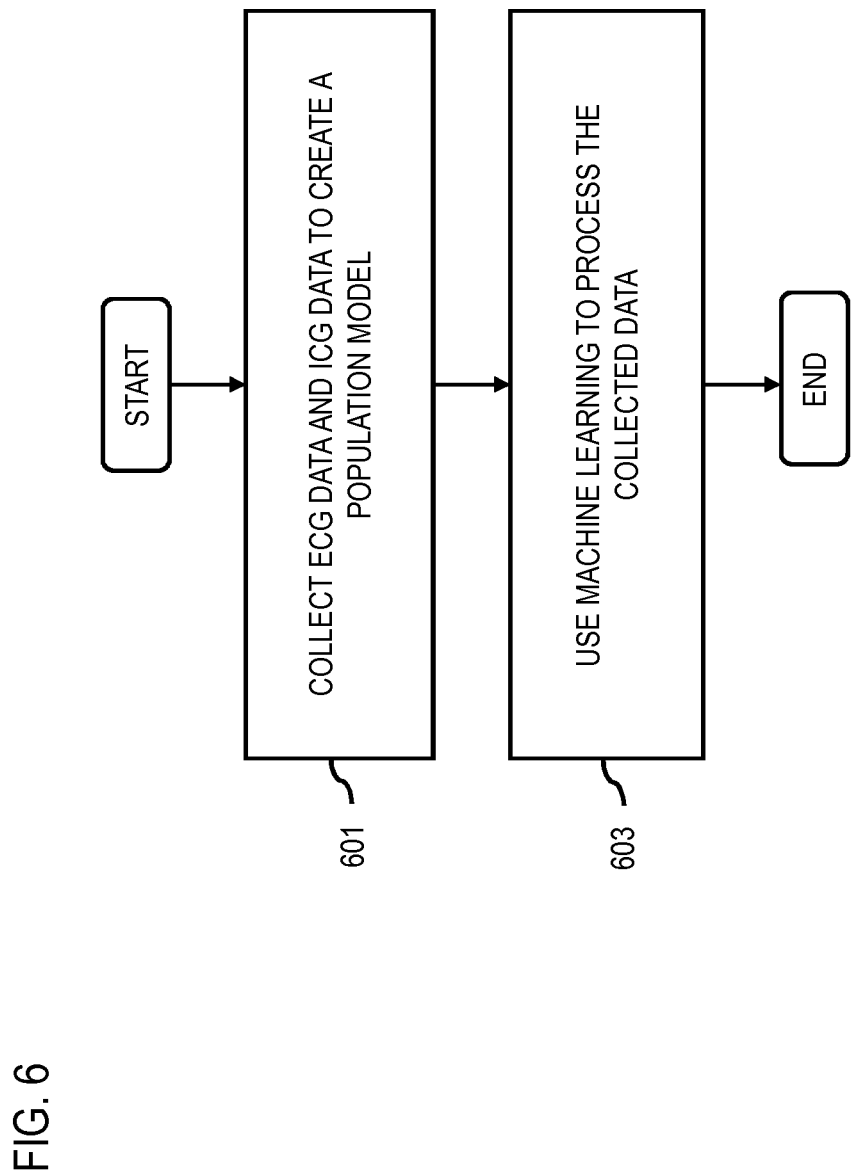
FIG. 6 is a flowchart of a process for processing historical ECG and ICG data from a population of patients using a machine learning process to set a predetermined duration and/or an electrical current level during an ICG signal measurement, according to one example embodiment.

FIG. 6 is a flowchart of a process for processing historical ECG and ICG data from a population of patients using a machine learning process to set a predetermined duration and/or an electrical current level during an ICG signal measurement, according to one example embodiment. In one embodiment, the synchronization platform 107 performs the process 600 and is implemented in, for instance, a chip set including a processor and a memory as shown in FIG. 12.

In step 601, the synchronization platform 107 collects ECG data and ICG data from a population of patients to create a population model. In one embodiment, the machine learning platform 113 may train a machine learning system with recorded ECG data and ICG data from multiple patients. In one scenario, continuous ECG data and ICG data is collected from multiple users, including users with heart condition. Then, the synchronization platform 107 finds per-person optimized currents and measurement periods by observing different features statistically typical for certain kinds of patients. In one example embodiment, the synchronization platform 107 may utilize randomized or semi-randomized measurement periods in addition to continuous measurements for collecting data to a personalized or a population model.

In step 603, the synchronization platform 107 processes the ECG data and the ICG data using a machine learning process to set a predetermined duration of the measurement of the ICG signal, an electrical current level to inject into the patient and/or the population of patients during the measurement of the ICG signal, or a combination thereof based on the population model. In one embodiment, machine learning is implemented to reduce the duty time and the total average current. In one scenario, a machine learning system is trained with recorded ECG data and ICG data from multiple patients to determine a per-person optimized current and a measurement period. In another embodiment, the machine learning model may be refined by exploring new settings with the current patients. In one example embodiment, an ICG device may inject an auxiliary current for a specific duration of 100 ms to reduce the duty time and the total average current. However, a significant amount of the population have the QRS duration between 100-124 ms without any cardiac disease. Given that the measurement period is pre-set to 100 ms, the B-point capture for the 2% of the population can be missed. As a result, the synchronization platform 107 may vary the measurement duration based on another feature within the ICG reading for accurately capturing the PEP for the 2% of the population. In one embodiment, the population model may be implemented without personalization, wherein the population model does not depend on a personalized model. In another embodiment, a personalized population model may be implemented by combining the population model and the personalized model.

Figure 7:
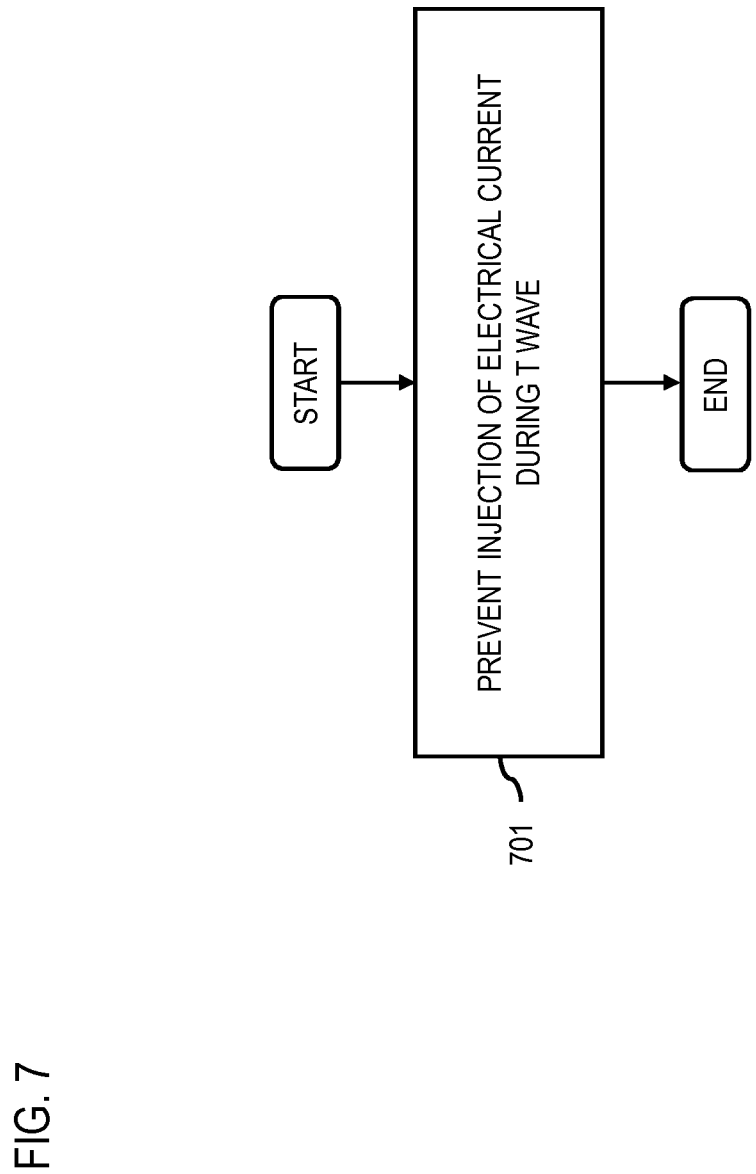
FIG. 7 is a flowchart of a process for discontinuing injection of electrical current during the T wave, according to one example embodiment.

FIG. 7 is a flowchart of a process for discontinuing injection of electrical current during the T wave, according to one example embodiment. In one embodiment, the synchronization platform 107 performs the process 700 and is implemented in, for instance, a chip set including a processor and a memory as shown in FIG. 12.

In step 701, the synchronization platform 107 prevents an injection of electrical current into the patient for the measurement of the ICG signal during the ventricular repolarization reflected by T wave. In one scenario, the synchronization platform 107 discontinues injection of a patient auxiliary current upon detecting a start of a T-wave because a patient's heart is extremely vulnerable to the patient auxiliary current when the T-wave begins. Any injection of an external current during the T-wave may cause arrhythmia. In one scenario, the T wave follows the S wave of the QRS complex, and the synchronization platform 107 stops or avoids injecting any current during the T wave, thereby improving patient safety.

Figure 8:
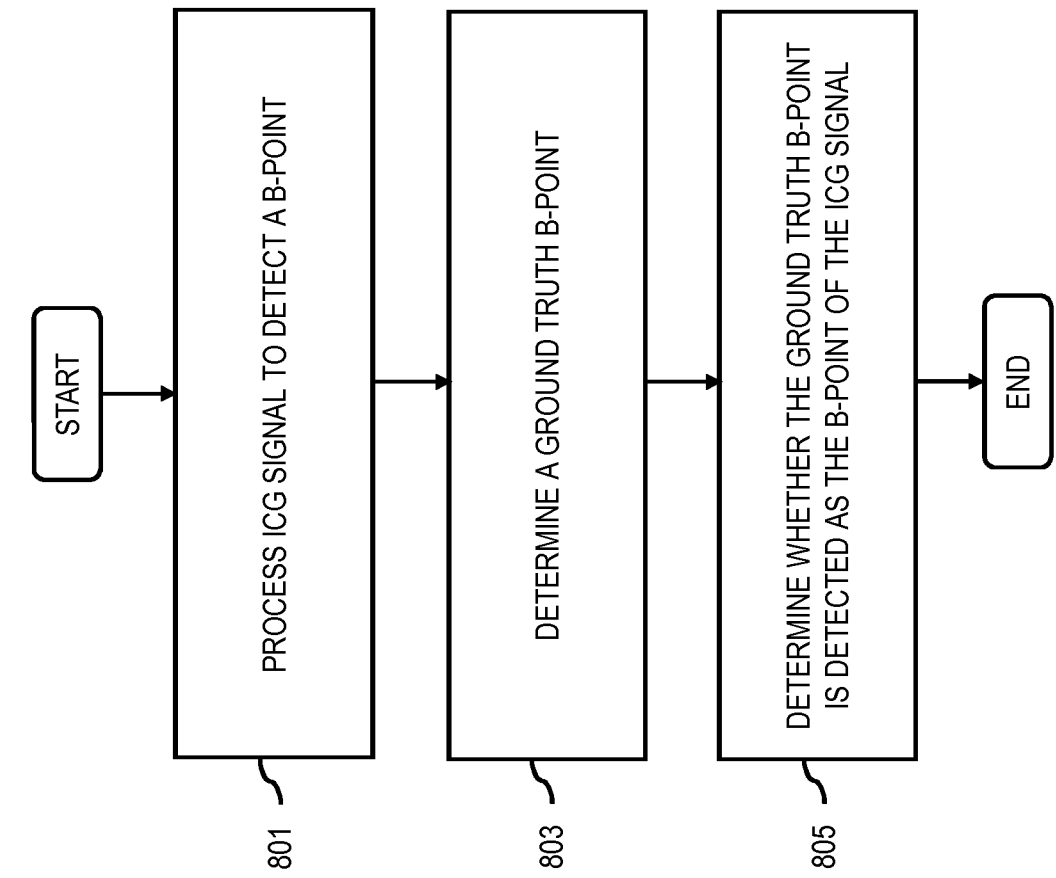
FIG. 8 is a flowchart of a process for determining a ground truth B-point, according to one example embodiment.

FIG. 8 is a flowchart of a process for determining a ground truth B-point, according to one example embodiment. In one embodiment, the synchronization platform 107 performs the process 800 and is implemented in, for instance, a chip set including a processor and a memory as shown in FIG. 12.

In step 801, the synchronization platform 107 processes the ICG signal to cause, at least in part, a detection of a B-point. In one scenario, a B-point is an interesting feature of an ICG signal that comes after the QRS complex of the ECG signal, and can be used in estimating the cardiac PEP.

In step 803, the synchronization platform 107 determines a ground truth B-point using a separate continuous ICG measurement of the patient. In one embodiment, an optimized duty cycle (e.g., ICG measurement period) and/or an optimized current level to be administered to at least one patient is calculated by the machine learning module 205 alone or in combination with the machine learning platform 113. In one embodiment, the optimized duty cycle and/or current level can be determined for individual patients via historical data and/or reinforcement learning.

In step 805, the synchronization platform 107 determines whether the ground truth B-point is detected as the B-point of the ICG signal to compute an optimal duration of a subsequent measurement of the ICG signal. In one embodiment, the machine learning process involves determining a ground truth for a feature of interest in the ICG signal using, e.g., a continuous ICG measurement (e.g., an ICG measurement which spans the entire cardiac cycle). For example, if the B-point (e.g., which indicates the end of the cardiac PEP) is the feature of interest in the ICG signal, the B-point can be detected in the continuous ICG data for the patients. The period for the start of the PEP to the ground truth B-point can be measured, with the period representing the optimized duty cycle. Similarly, current levels can be varied to find an optimized current level that provides sufficient signal quality (e.g., based on signal to noise ratio or any other measure of signal quality) that can still detect the feature of interest in the ICG signal based on the ground truth. In this case, a ground truth detection of the ICG feature of interest (e.g., the B-point) can be made at a higher current, and then subsequently lower currents can be measured in specific individual to determine the lowest current that can detect the feature as the optimized current.

Figure 9A:
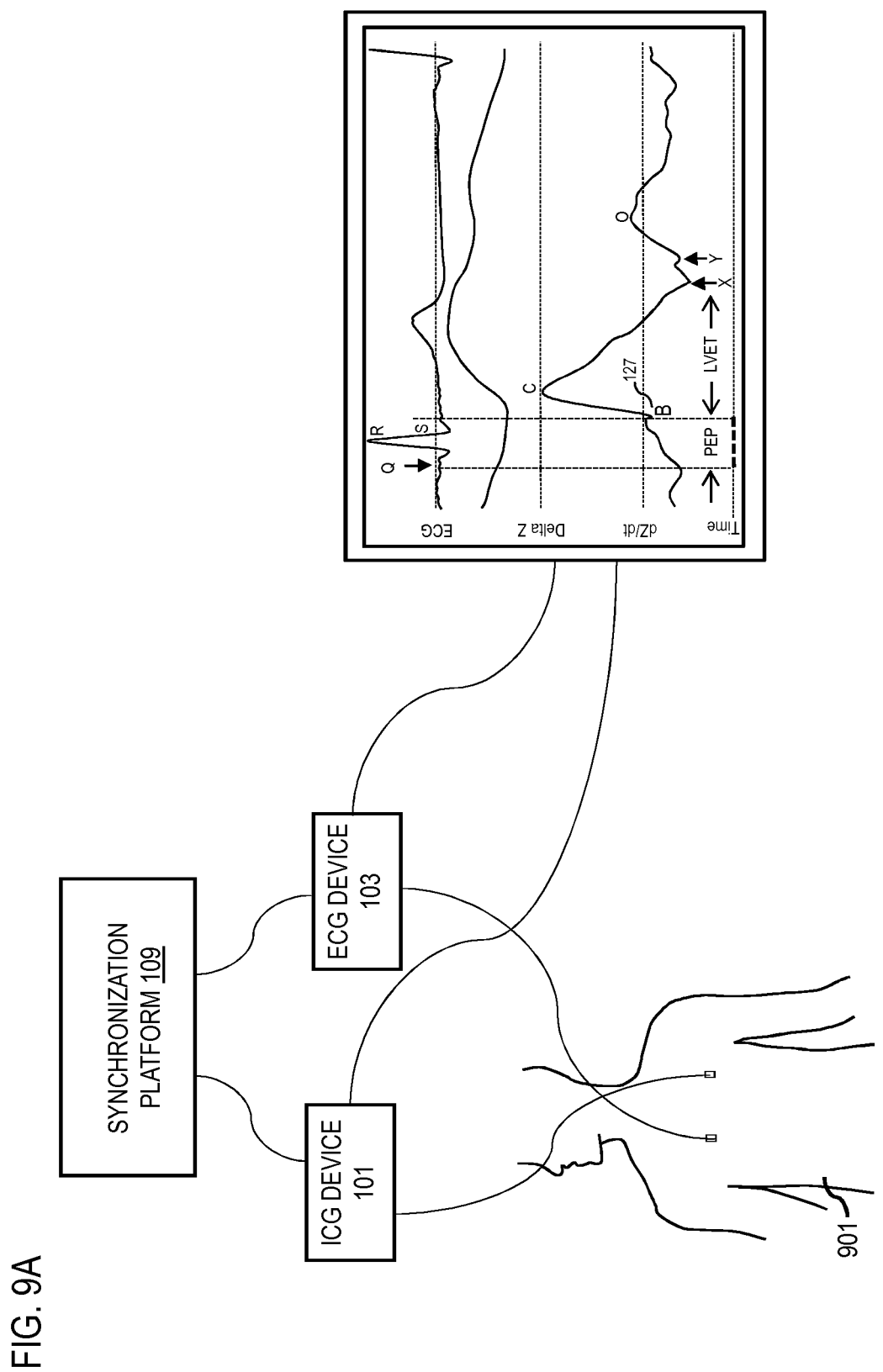
FIG. 9A is a diagram that represent a scenario wherein an ECG signal and an ICG signal of a patient is synchronized to reduce patient auxiliary current, according to one example embodiment.

FIG. 9A is a diagram that represent a scenario wherein an ECG signal and an ICG signal of a patient is synchronized to reduce patient auxiliary current, according to one example embodiment. In FIG. 9A, an ICG electrodes and an ECG electrodes are placed on a patient's body 901 (e.g., thorax) to measure various properties of the patient's heart. The ECG device 103 can detect a beginning of an ECG feature for a heartbeat detected in a corresponding ECG signal, and then trigger the ICG device 101 to inject an electric current through the patient's body via the electrodes continuously for the duration of the measurement. Measurements of variations in the impedance of the injected current as it travels through the thorax over time are then taken to characterize various properties of the heart. An ICG device 101 and an ECG device 103 simultaneously collect ECG and ICG signal to monitor the heart and vascular system of the patient. In one scenario, the ECG signal includes a QRS complex. The QRS complex (including a Q wave, an R wave, and an S wave) corresponds to a current that causes contraction of the left and right ventricles, which is typically much more forceful than that of the atria and involves more muscle mass, thus resulting in a greater ECG deflection. The Q wave represents the small horizontal (left to right) current as the action potential travels through the interventricular septum. The R and S waves indicate contraction of the myocardium. On the other hand, an ICG signal includes a B-point. The B-point represents the opening of the aortic valve, when the blood suddenly shoots out of the already contracted left ventricle into the aorta. In one embodiment, the synchronization platform 107 initiates measurement of an ICG signal upon detecting an ECG feature (e.g., start of the Q wave) for a predetermined period of time (e.g., 100 ms) that is estimated to encompass the cardiac PEP for a typical patient. In one scenario, the PEP is the period between when the ventricular contraction occurs and the semilunar valves open and blood ejection into the aorta commences. In one embodiment, the synchronization platform 107 may measure an ICG signal only during an interesting time period, for example, B-point is an interesting feature of the ICG signal because B-point can estimate the PEP. The B-point comes after the QRS complex hence the ICG measurement can be very short. For example, the ICG measurement can be 100 ms time interval between the heart beats. If the heart rate is 60 bpm then the duty cycle of the ICG would be only 10% for the heart rate of 60 bpm. Therefore, the RMS of the ICG calculated over the predetermined period is significantly reduced. For example, the 1 mA peak current injected during the measurement period is effectively reduced to approximately 320 uA RMS, thereby achieving the advantageous result of reducing the patient 901's overall auxiliary current exposure.

Figure 9B:
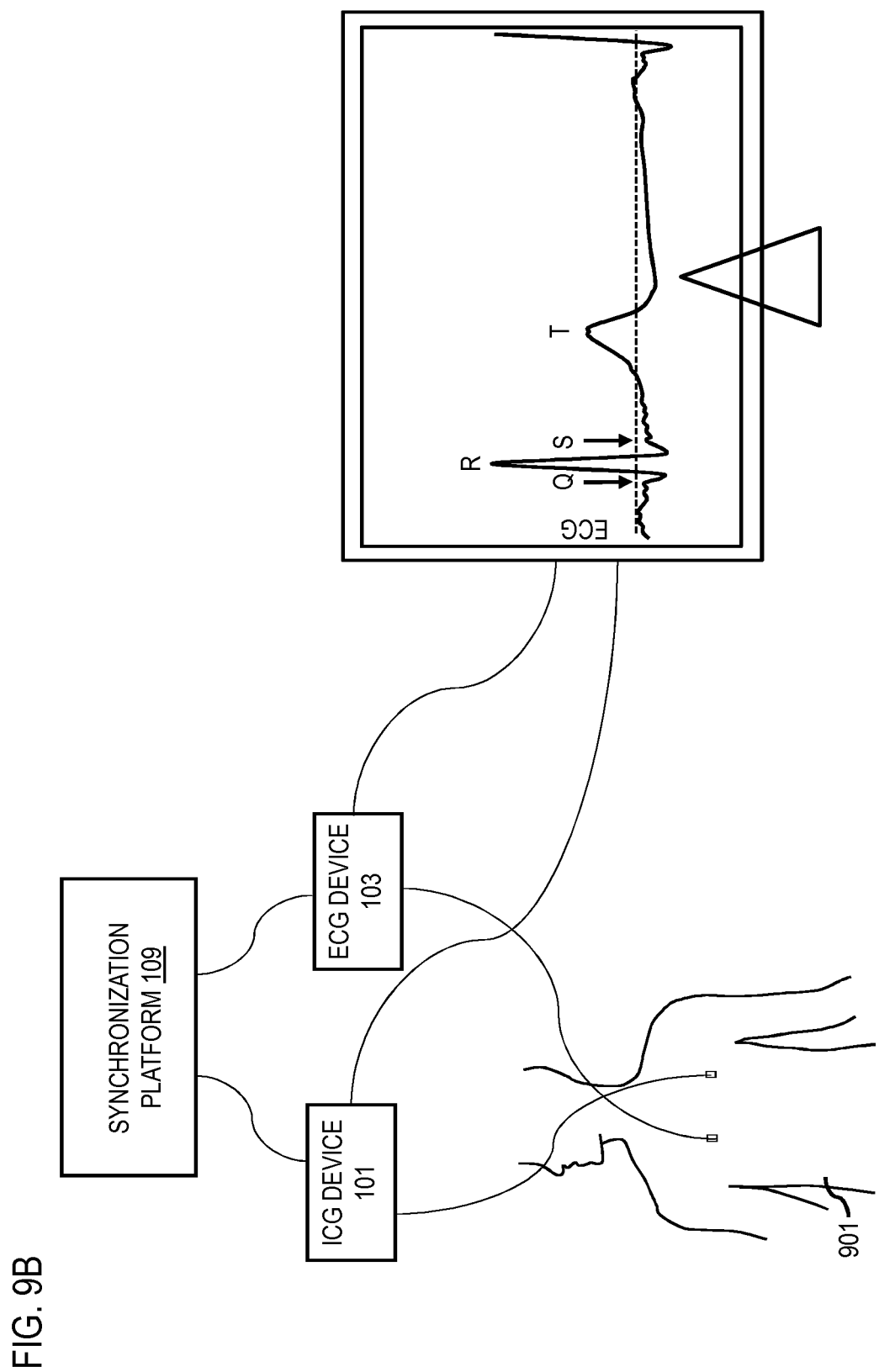
FIG. 9B is a diagram that represents a scenario wherein the synchronization platform 107 stops injecting any electrical current during the T wave, according to one example embodiment.

FIG. 9B is a diagram that represents a scenario wherein the synchronization platform 107 stops injecting any electrical current during the T wave, according to one example embodiment. In one embodiment, the detection module 201 of the synchronization platform 107 detects a specific ECG features (e.g., a beginning of a T wave) that have been correlated with portions of an ICG signal that are known to be of interest. In one scenario, the T wave follows the QRS complex, and represents repolarization of the ventricles. In one embodiment, the synchronization platform 107 discontinues injecting any electrical current upon detecting a beginning of a T wave which comes roughly 100 ms after the S wave of the QRS complex. In one scenario, a patient's heart is the most vulnerable to any current when the T wave begins, for example, any external current may cause arrhythmia. As a result, the synchronization platform 107 discontinues any current flow during the T wave to improve patient safety.

Figure 10:
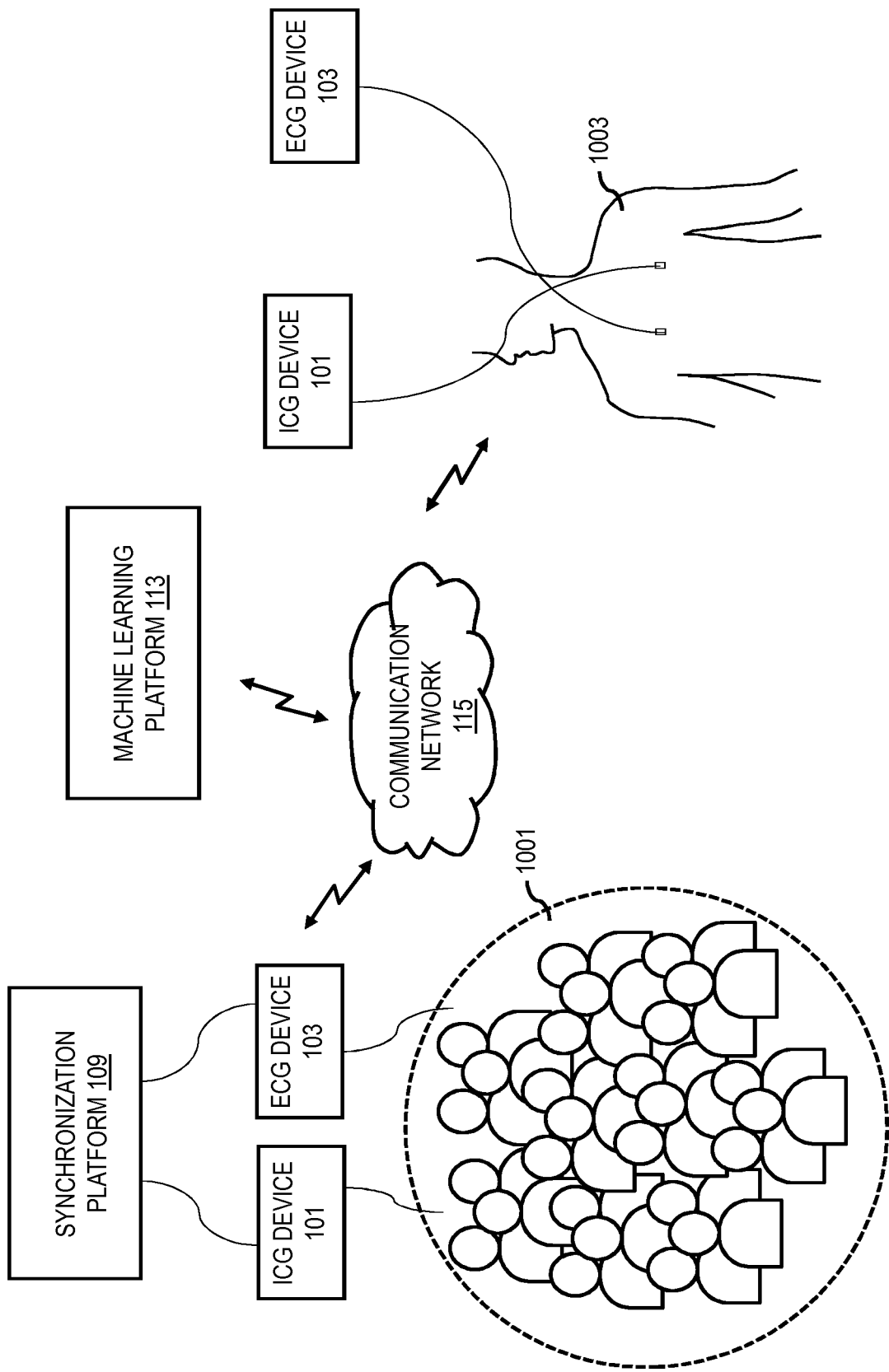
FIG. 10 is a diagram that represents a scenario wherein features statistically standard for a population of patients are observed to create a population model, according to one example embodiment.

FIG. 10 is a diagram that represents a scenario wherein features statistically standard for a population of patients are observed to create a population model, according to one example embodiment. In one scenario, an ICG device 101 and an ECG device 103 simultaneously collects ECG and ICG signals from a particular group of patients 1001. The synchronization platform 107 connected to a machine learning platform 113 over the communication network 115 processes the ECG and ICG signals to set parameters for duty time (e.g., ICG measurement start time, stop time, and/or duration) and/or current injection settings (e.g., level of injection current) for a population of patients and/or individual classes of patients. In one example embodiment, an ICG device 101 injects 1 mA current for a duration of 100 ms that is synchronized to an ECG feature within the ECG signal into a patient 1003 during cardiac cycles. However, the synchronization platform 107 connected to a machine learning platform 113 determines the ICG duration for the group of patients 1001 to be 120 ms time interval between the heart beats. Then, synchronization platform 107 connected to a machine learning platform 113 refines the stored ECG and ICG data (e.g., the initial ICG measurement of 100 ms time interval between the heart beats is updated to 120 ms time interval between the heart beats).

The processes described herein for synchronizing an ICG measurement period with an ECG signal to reduce patient auxiliary current may be advantageously implemented via software, hardware, firmware or a combination of software and/or firmware and/or hardware. For example, the processes described herein, may be advantageously implemented via processor(s), Digital Signal Processing (DSP) chip, an Application Specific Integrated Circuit (ASIC), Field Programmable Gate Arrays (FPGAs), etc. Such exemplary hardware for performing the described functions is detailed below.

Figure 11:
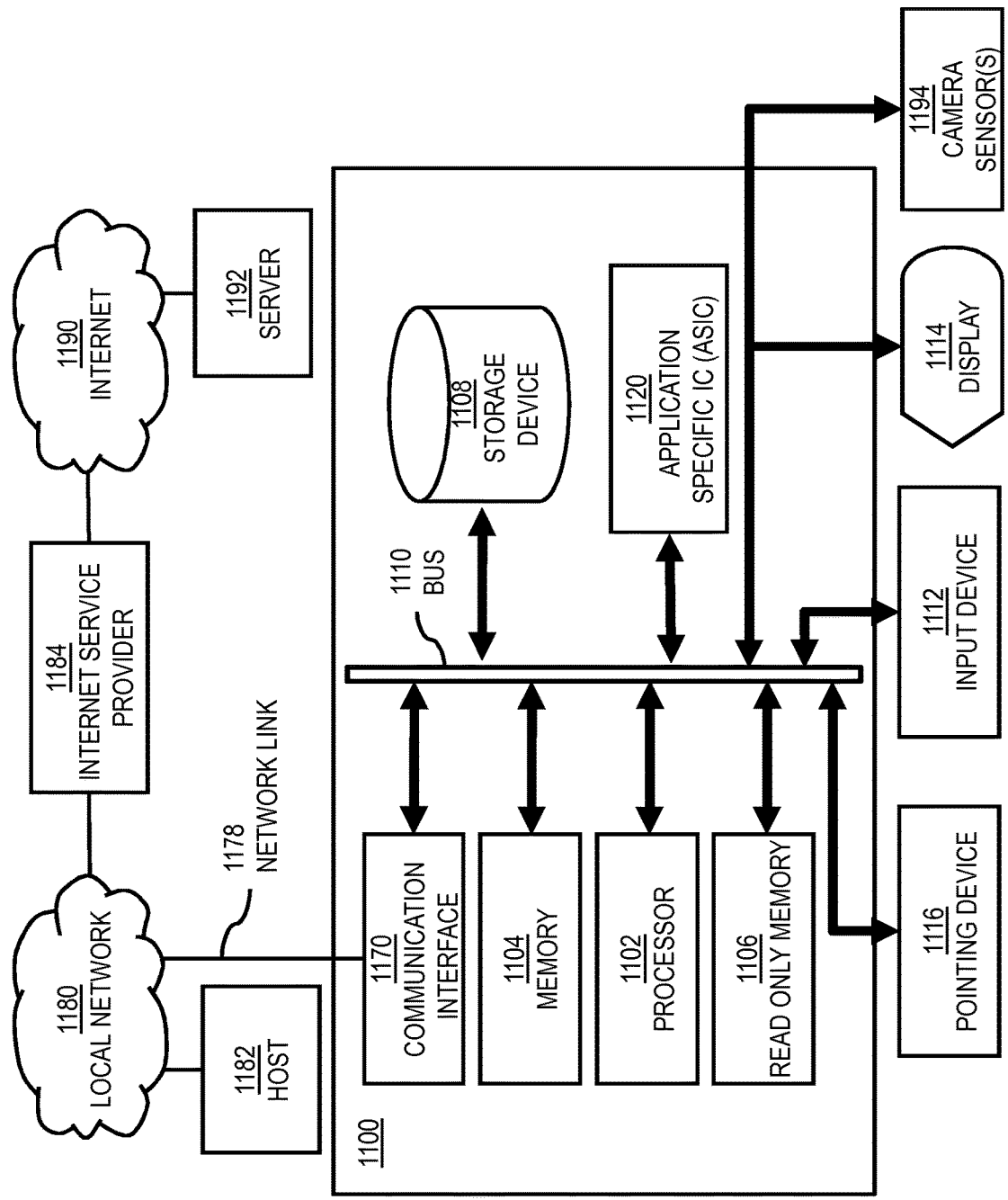
FIG. 11 is a diagram of hardware that can be used to implement an embodiment of the invention.

FIG. 11 illustrates a computer system 1100 upon which an embodiment of the invention may be implemented. Although computer system 1100 is depicted with respect to a particular device or equipment, it is contemplated that other devices or equipment (e.g., network elements, servers, etc.) within FIG. 11 can deploy the illustrated hardware and components of system 1100. Computer system 1100 is programmed (e.g., via computer program code or instructions) to synchronize an ICG measurement period with an ECG signal to reduce patient auxiliary current as described herein and includes a communication mechanism such as a bus 1110 for passing information between other internal and external components of the computer system 1100. Information (also called data) is represented as a physical expression of a measurable phenomenon, typically electric voltages, but including, in other embodiments, such phenomena as magnetic, electromagnetic, pressure, chemical, biological, molecular, atomic, sub-atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1100, or a portion thereof, constitutes a means for performing one or more steps of synchronizing an ICG measurement period with an ECG signal to reduce patient auxiliary current.

A bus 1110 includes one or more parallel conductors of information so that information is transferred quickly among devices coupled to the bus 1110. One or more processors 1102 for processing information are coupled with the bus 1110.

A processor (or multiple processors) 1102 performs a set of operations on information as specified by computer program code related to synchronizing an ICG measurement period with an ECG signal to reduce patient auxiliary current. The computer program code is a set of instructions or statements providing instructions for the operation of the processor and/or the computer system to perform specified functions. The code, for example, may be written in a computer programming language that is compiled into a native instruction set of the processor. The code may also be written directly using the native instruction set (e.g., machine language). The set of operations include bringing information in from the bus 1110 and placing information on the bus 1110. The set of operations also typically include comparing two or more units of information, shifting positions of units of information, and combining two or more units of information, such as by addition or multiplication or logical operations like OR, exclusive OR (XOR), and AND. Each operation of the set of operations that can be performed by the processor is represented to the processor by information called instructions, such as an operation code of one or more digits. A sequence of operations to be executed by the processor 1102, such as a sequence of operation codes, constitute processor instructions, also called computer system instructions or, simply, computer instructions. Processors may be implemented as mechanical, electrical, magnetic, optical, chemical, or quantum components, among others, alone or in combination.

Computer system 1100 also includes a memory 1104 coupled to bus 1110. The memory 1104, such as a random access memory (RAM) or any other dynamic storage device, stores information including processor instructions for synchronizing an ICG measurement period with an ECG signal to reduce patient auxiliary current. Dynamic memory allows information stored therein to be changed by the computer system 1100. RAM allows a unit of information stored at a location called a memory address to be stored and retrieved independently of information at neighboring addresses. The memory 1104 is also used by the processor 1102 to store temporary values during execution of processor instructions. The computer system 1100 also includes a read only memory (ROM) 1106 or any other static storage device coupled to the bus 1110 for storing static information, including instructions, that is not changed by the computer system 1100. Some memory is composed of volatile storage that loses the information stored thereon when power is lost. Also coupled to bus 1110 is a non-volatile (persistent) storage device 1108, such as a magnetic disk, optical disk or flash card, for storing information, including instructions, that persists even when the computer system 1100 is turned off or otherwise loses power.

Information, including instructions for synchronizing an ICG measurement period with an ECG signal to reduce patient auxiliary current, is provided to the bus 1110 for use by the processor from an external input device 1112, such as a keyboard containing alphanumeric keys operated by a human user, a microphone, an Infrared (IR) remote control, a joystick, a game pad, a stylus pen, a touch screen, or a sensor. A sensor detects conditions in its vicinity and transforms those detections into physical expression compatible with the measurable phenomenon used to represent information in computer system 1100. Other external devices coupled to bus 1110, used primarily for interacting with humans, include a display device 1114, such as a cathode ray tube (CRT), a liquid crystal display (LCD), a light emitting diode (LED) display, an organic LED (OLED) display, a plasma screen, or a printer for presenting text or images, and a pointing device 1116, such as a mouse, a trackball, cursor direction keys, or a motion sensor, for controlling a position of a small cursor image presented on the display 1114 and issuing commands associated with graphical elements presented on the display 1114, and one or more camera sensors 1194 for capturing, recording and causing to store one or more still and/or moving images (e.g., videos, movies, etc.) which also may comprise audio recordings. In some embodiments, for example, in embodiments in which the computer system 1100 performs all functions automatically without human input, one or more of external input device 1112, display device 1114 and pointing device 1116 may be omitted.

In the illustrated embodiment, special purpose hardware, such as an application specific integrated circuit (ASIC) 1120, is coupled to bus 1110. The special purpose hardware is configured to perform operations not performed by processor 1102 quickly enough for special purposes. Examples of ASICs include graphics accelerator cards for generating images for display 1114, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1100 also includes one or more instances of a communications interface 1170 coupled to bus 1110. Communication interface 1170 provides a one-way or two-way communication coupling to a variety of external devices that operate with their own processors, such as printers, scanners and external disks. In general the coupling is with a network link 1178 that is connected to a local network 1180 to which a variety of external devices with their own processors are connected. For example, communication interface 1170 may be a parallel port or a serial port or a universal serial bus (USB) port on a personal computer. In some embodiments, communications interface 1170 is an integrated services digital network (ISDN) card or a digital subscriber line (DSL) card or a telephone modem that provides an information communication connection to a corresponding type of telephone line. In some embodiments, a communication interface 1170 is a cable modem that converts signals on bus 1110 into signals for a communication connection over a coaxial cable or into optical signals for a communication connection over a fiber optic cable. As another example, communications interface 1170 may be a local area network (LAN) card to provide a data communication connection to a compatible LAN, such as Ethernet. Wireless links may also be implemented. For wireless links, the communications interface 1170 sends or receives or both sends and receives electrical, acoustic or electromagnetic signals, including infrared and optical signals, that carry information streams, such as digital data. For example, in wireless handheld devices, such as mobile telephones like cell phones, the communications interface 1170 includes a radio band electromagnetic transmitter and receiver called a radio transceiver. In certain embodiments, the communications interface 1170 enables connection to the communication network 115 for synchronizing an ICG measurement period with an ECG signal to reduce patient auxiliary current to the ICG device 101 and/or ECG device 103.

The term "computer-readable medium" as used herein refers to any medium that participates in providing information to processor 1102, including instructions for execution. Such a medium may take many forms, including, but not limited to computer-readable storage medium (e.g., non-volatile media, volatile media), and transmission media. Non-transitory media, such as non-volatile media, include, for example, optical or magnetic disks, such as storage device 1108. Volatile media include, for example, dynamic memory 1104. Transmission media include, for example, twisted pair cables, coaxial cables, copper wire, fiber optic cables, and carrier waves that travel through space without wires or cables, such as acoustic waves and electromagnetic waves, including radio, optical and infrared waves. Signals include man-made transient variations in amplitude, frequency, phase, polarization or other physical properties transmitted through the transmission media. Common forms of computer-readable media include, for example, a floppy disk, a flexible disk, hard disk, magnetic tape, any other magnetic medium, a CD-ROM, CDRW, DVD, any other optical medium, punch cards, paper tape, optical mark sheets, any other physical medium with patterns of holes or other optically recognizable indicia, a RAM, a PROM, an EPROM, a FLASH-EPROM, an EEPROM, a flash memory, any other memory chip or cartridge, a carrier wave, or any other medium from which a computer can read. The term computer-readable storage medium is used herein to refer to any computer-readable medium except transmission media.

Logic encoded in one or more tangible media includes one or both of processor instructions on a computer-readable storage media and special purpose hardware, such as ASIC 1120.

Network link 1178 typically provides information communication using transmission media through one or more networks to other devices that use or process the information. For example, network link 1178 may provide a connection through local network 1180 to a host computer 1182 or to equipment 1184 operated by an Internet Service Provider (ISP). ISP equipment 1184 in turn provides data communication services through the public, world-wide packet-switching communication network of networks now commonly referred to as the Internet 1190.

A computer called a server host 1192 connected to the Internet hosts a process that provides a service in response to information received over the Internet. For example, server host 1192 hosts a process that provides information representing video data for presentation at display 1114. It is contemplated that the components of system 1100 can be deployed in various configurations within other computer systems, e.g., host 1182 and server 1192.

At least some embodiments of the invention are related to the use of computer system 1100 for implementing some or all of the techniques described herein. According to one embodiment of the invention, those techniques are performed by computer system 1100 in response to processor 1102 executing one or more sequences of one or more processor instructions contained in memory 1104. Such instructions, also called computer instructions, software and program code, may be read into memory 1104 from another computer-readable medium such as storage device 1108 or network link 1178. Execution of the sequences of instructions contained in memory 1104 causes processor 1102 to perform one or more of the method steps described herein. In alternative embodiments, hardware, such as ASIC 1120, may be used in place of or in combination with software to implement the invention. Thus, embodiments of the invention are not limited to any specific combination of hardware and software, unless otherwise explicitly stated herein.

The signals transmitted over network link 1178 and other networks through communications interface 1170, carry information to and from computer system 1100. Computer system 1100 can send and receive information, including program code, through the networks 1180, 1190 among others, through network link 1178 and communications interface 1170. In an example using the Internet 1190, a server host 1192 transmits program code for a particular application, requested by a message sent from computer 1100, through Internet 1190, ISP equipment 1184, local network 1180 and communications interface 1170. The received code may be executed by processor 1102 as it is received, or may be stored in memory 1104 or in storage device 1108 or any other non-volatile storage for later execution, or both. In this manner, computer system 1100 may obtain application program code in the form of signals on a carrier wave.

Various forms of computer readable media may be involved in carrying one or more sequence of instructions or data or both to processor 1102 for execution. For example, instructions and data may initially be carried on a magnetic disk of a remote computer such as host 1182. The remote computer loads the instructions and data into its dynamic memory and sends the instructions and data over a telephone line using a modem. A modem local to the computer system 1100 receives the instructions and data on a telephone line and uses an infra-red transmitter to convert the instructions and data to a signal on an infra-red carrier wave serving as the network link 1178. An infrared detector serving as communications interface 1170 receives the instructions and data carried in the infrared signal and places information representing the instructions and data onto bus 1110. Bus 1110 carries the information to memory 1104 from which processor 1102 retrieves and executes the instructions using some of the data sent with the instructions. The instructions and data received in memory 1104 may optionally be stored on storage device 1108, either before or after execution by the processor 1102.

FIG. 12 illustrates a chip set or chip 1200 upon which an embodiment of the invention may be implemented. Chip set 1200 is programmed to synchronize an ICG measurement period with an ECG signal to reduce patient auxiliary current as described herein and includes, for instance, the processor and memory components described with respect to FIG. 11 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set 1200 can be implemented in a single chip. It is further contemplated that in certain embodiments the chip set or chip 1200 can be implemented as a single "system on a chip." It is further contemplated that in certain embodiments a separate ASIC would not be used, for example, and that all relevant functions as disclosed herein would be performed by a processor or processors. Chip set or chip 1200, or a portion thereof, constitutes a means for performing one or more steps of providing user interface navigation information associated with the availability of functions. Chip set or chip 1200, or a portion thereof, constitutes a means for performing one or more steps of synchronizing an ICG measurement period with an ECG signal to reduce patient auxiliary current.

In one embodiment, the chip set or chip 1200 includes a communication mechanism such as a bus 1201 for passing information among the components of the chip set 1200. A processor 1203 has connectivity to the bus 1201 to execute instructions and process information stored in, for example, a memory 1205. The processor 1203 may include one or more processing cores with each core configured to perform independently. A multi-core processor enables multiprocessing within a single physical package. Examples of a multi-core processor include two, four, eight, or greater numbers of processing cores. Alternatively or in addition, the processor 1203 may include one or more microprocessors configured in tandem via the bus 1201 to enable independent execution of instructions, pipelining, and multithreading. The processor 1203 may also be accompanied with one or more specialized components to perform certain processing functions and tasks such as one or more digital signal processors (DSP) 1207, or one or more application-specific integrated circuits (ASIC) 1209. A DSP 1207 typically is configured to process real-world signals (e.g., sound) in real time independently of the processor 1203. Similarly, an ASIC 1209 can be configured to performed specialized functions not easily performed by a more general purpose processor. Other specialized components to aid in performing the inventive functions described herein may include one or more field programmable gate arrays (FPGA), one or more controllers, or one or more other special-purpose computer chips.

In one embodiment, the chip set or chip 1200 includes merely one or more processors and some software and/or firmware supporting and/or relating to and/or for the one or more processors.

The processor 1203 and accompanying components have connectivity to the memory 1205 via the bus 1201. The memory 1205 includes both dynamic memory (e.g., RAM, magnetic disk, writable optical disk, etc.) and static memory (e.g., ROM, CD-ROM, etc.) for storing executable instructions that when executed perform the inventive steps described herein to synchronize an ICG measurement period with an ECG signal to reduce patient auxiliary current. The memory 1205 also stores the data associated with or generated by the execution of the inventive steps.

While the invention has been described in connection with a number of embodiments and implementations, the invention is not so limited but covers various obvious modifications and equivalent arrangements, which fall within the purview of the appended claims. Although features of the invention are expressed in certain combinations among the claims, it is contemplated that these features can be arranged in any combination and order.

What is claimed is:

1. A method comprising:
    measuring an electrocardiography (ECG) signal of a patient via an ECG device;
    processing the ECG signal to cause, at least in part, a detection of one or more ECG features of the signal;
    synchronizing a start, a stop, or a combination thereof of a measurement of an impedance cardiography (ICG) signal of the patient via an ICG device based, at least in part, on the detection of the one or more ECG features to reduce patient auxiliary current; and
    setting a predetermined duration for the measurement of the ICG signal, based on an electrical current level injected into the patient during the measurement of the ICG signal,
    wherein the measurement of the ICG signal includes injecting an electrical current into the patient for a duration of the measurement of the ICG signal.

2. A method according to claim 1, wherein the one or more ECG features is a pace signal of the ECG device, and wherein the start, the stop, or a combination thereof of the measurement of the ICG signal is synchronized to the pace signal.

3. A method according to claim 1, wherein the ECG feature is a Q wave, the method further comprising:
    synchronizing the start of the measurement of the ICG signal based on a detected start of the Q wave.

4. A method according to claim 3, further comprising:
    synchronizing the stop of the measurement of the ICG signal to a predetermined duration following the start of the measurement of the ICG signal.

5. A method according to claim 1, further comprising:
    collecting historical ECG data and historical ICG data for the patient to create an individual model; and
    processing the historical ECG data and the historical ICG data using a machine learning process to set a predetermined duration of the measurement of the ICG signal, an electrical current level to inject into the patient during the measurement of the ICG signal, or a combination thereof based on the individual model.

6. A method according to claim 1, further comprising:
    collecting ECG data and ICG data from a population of patients to create a population model; and
    processing the ECG data and the ICG data using a machine learning process to set a predetermined duration of the measurement of the ICG signal, an electrical current level to inject into the patient and/or a population of patients during the measurement of the ICG signal, or a combination thereof based on the population model.

7. A method according to claim 1, wherein the one or more ECG features is a T wave, the method further comprising:
preventing an injection of electrical current into the patient for the measurement of the ICG signal during a ventricular repolarization reflected by the T wave.

8. A method according to claim 1, further comprising:
processing the ICG signal to cause, at least in part, a detection of a B-point; and
determining a ground truth B-point using a separate continuous ICG measurement of the patient;
determining whether the ground truth B-point is detected as the B-point of the ICG signal to compute an optimal duration of a subsequent measurement of the ICG signal,
wherein the measurement of the ICG signal includes injecting an electrical current into the patient for a duration of the measurement.

9. An apparatus comprising:
at least one processor; and
at least one memory including computer program code for one or more programs, the at least one memory and the computer program code configured to, with the at least one processor, cause the apparatus to perform at least the following;
measure an electrocardiography (ECG) signal of a patient, via an ECG device configured to measure an ECG signal;
process the ECG signal to cause, at least in part, a detection of one or more ECG features of the signal;
synchronize a start, a stop, or a combination thereof of a measurement of an impedance cardiography (ICG) signal of the patient, via an ICG device configured to measure an ICG signal, based, at least in part, on the detection of the one or more ECG features to reduce patient auxiliary current; and
setting a predetermined duration for the measurement of the ICG signal, based on an electrical current level injected into the patient during the measurement of the ICG signal,
wherein the measurement of the ICG signal includes injecting, via the ICG device, an electrical current into the patient for a duration of the measurement of the ICG signal.

10. An apparatus according to claim 9, wherein the one or more ECG features is a pace signal of the ECG device, and wherein the start, the stop, or a combination thereof of the measurement of the ICG signal is synchronized to the pace signal.

11. An apparatus according to claim 9, wherein the ECG feature is a Q wave, wherein the apparatus is further caused to:
synchronize the start of the measurement of the ICG signal based on a detected start of the Q wave.

12. An apparatus according to claim 11, wherein the apparatus is further caused to
synchronize the stop of the measurement of the ICG signal to a predetermined duration following the start of the measurement of the ICG signal.

13. An apparatus according to claim 11, wherein the apparatus is further caused to:
synchronize the stop of the measurement of the ICG signal to another ECG feature detected subsequent to the Q wave,
wherein the another ECG feature includes, at least in part, an end of a QRS complex, an S wave, or a beginning of a T wave.

14. An apparatus according to claim 9, wherein the apparatus is further caused to:
collect historical ECG data and historical ICG data for the patient to create an individual model; and
process the historical ECG data and the historical ICG data using a machine learning process to set a predetermined duration of the measurement of the ICG signal, an electrical current level to inject into the patient during the measurement of the ICG signal, or a combination thereof based on the individual model.

15. An apparatus according to claim 9, wherein the apparatus is further caused to:
collect ECG data and ICG data from a population of patients to create a population model; and
process the ECG data and the ICG data using a machine learning process to set a predetermined duration of the measurement of the ICG signal, an electrical current level to inject into the patient and/or a population of patients during the measurement of the ICG signal, or a combination thereof based on the population model.

16. An apparatus according to claim 9, wherein the one or more ECG features is a T wave, wherein the apparatus is further caused to:
prevent an injection of electrical current into the patient for the measurement of the ICG signal during a ventricular repolarization reflected by the T wave.

17. An apparatus according to claim 9, wherein the apparatus is further caused to:
process the ICG signal to cause, at least in part, a detection of a B-point; and
determine a ground truth B-point using a separate continuous ICG measurement of the patient;
determine whether the ground truth B-point is detected as the B-point of the ICG signal to compute an optimal duration of a subsequent measurement of the ICG signal,
wherein the measurement of the ICG signal includes injecting an electrical current into the patient for a duration of the measurement.

18. An apparatus according to claim 9, wherein the ECG device and the ICG device are a part of a single device.

* * * * *